United States Patent [19]
Duchon et al.

[11] Patent Number: 6,099,502
[45] Date of Patent: Aug. 8, 2000

[54] DUAL PORT SYRINGE

[75] Inventors: Doug Duchon, Chanhassen; Thomas Paulson, Minneapolis; Vince Copa, St. Paul; Robert F. Wilson, Shoreview; Jiyan Liu, Roseville, all of Minn.

[73] Assignee: Acist Medical Systems, Inc., Eden Prairie, Minn.

[21] Appl. No.: 08/957,228

[22] Filed: Oct. 24, 1997

Related U.S. Application Data

[63] Continuation-in-part of application No. 08/946,667, Oct. 7, 1997, Pat. No. 5,882,343, which is a continuation of application No. 08/426,149, Apr. 20, 1995, abandoned.

[51] Int. Cl.[7] .......................... A61M 37/00; A61M 5/00; A61M 1/00
[52] U.S. Cl. .......................... 604/131; 604/232; 604/151; 128/DIG. 12
[58] Field of Search .................. 604/52, 53, 131, 604/152, 155, 246, 247, 283, 256, 284, 228, 232, 234, 151, 154, 513; 128/DIG. 12

[56] References Cited

U.S. PATENT DOCUMENTS

| | | |
|---|---|---|
| 1,495,924 | 5/1924 | Quale ........................................ 604/232 |
| 1,704,921 | 3/1929 | Nicoll ....................................... 604/232 |
| 3,734,258 | 5/1973 | Roob . |
| 3,768,484 | 10/1973 | Gawura . |
| 3,768,518 | 10/1973 | Roth et al. . |
| 3,910,466 | 10/1975 | Collar . |
| 3,957,052 | 5/1976 | Topham . |
| 4,000,685 | 1/1977 | Montalvo, Jr. . |
| 4,267,836 | 5/1981 | Whitney et al. . |
| 4,366,831 | 1/1983 | Scott . |
| 4,469,481 | 9/1984 | Kobayashi . |
| 4,475,666 | 10/1984 | Bilbrey et al. . |
| 4,502,488 | 3/1985 | Degironimo et al. . |
| 4,585,941 | 4/1986 | Bergner . |
| 4,594,073 | 6/1986 | Stine ........................................ 604/187 |
| 4,619,646 | 10/1986 | Hernandez et al. ..................... 604/154 |
| 4,677,980 | 7/1987 | Reilly et al. ............................ 604/154 |
| 4,812,724 | 3/1989 | Langer et al. . |
| 4,842,576 | 6/1989 | Lysaght et al. . |
| 4,865,581 | 9/1989 | Lundquist et al. . |
| 4,903,705 | 2/1990 | Imamura et al. . |
| 4,921,488 | 5/1990 | Maitz et al. . |
| 5,006,110 | 4/1991 | Garrison et al. ......................... 604/65 |
| 5,059,174 | 10/1991 | Vaillancourt . |
| 5,084,011 | 1/1992 | Grady . |
| 5,084,017 | 1/1992 | Maffetone ............................. 604/110 |
| 5,178,609 | 1/1993 | Ishikawa ............................... 604/131 |
| 5,246,012 | 9/1993 | Strickland . |
| 5,340,364 | 8/1994 | Ghelli et al. . |
| 5,342,298 | 8/1994 | Michaels et al. . |
| 5,383,858 | 1/1995 | Reilly et al. ............................ 604/152 |
| 5,417,213 | 5/1995 | Prince . |
| 5,423,746 | 6/1995 | Burkett et al. . |
| 5,472,403 | 12/1995 | Cornacchia et al. . |
| 5,485,831 | 1/1996 | Holdsworth et al. . |

(List continued on next page.)

FOREIGN PATENT DOCUMENTS

| | | |
|---|---|---|
| 0 554 716 A1 | 8/1993 | European Pat. Off. . |
| 0 567 944 A1 | 11/1993 | European Pat. Off. . |
| 2 153 445 | 8/1985 | United Kingdom . |
| WO 88/03815 | 6/1988 | WIPO . |
| WO 93/15658 | 8/1993 | WIPO . |
| WO96/32975 | 10/1996 | WIPO . |
| WO97/07841 | 3/1997 | WIPO . |

*Primary Examiner*—Sharon Kennedy
*Attorney, Agent, or Firm*—Oppenheimer Wolff & Donnelly, LLP

[57] ABSTRACT

A dual port syringe has an upper port for connection to a fluid reservoir and a lower port for delivery of the medical fluid under pressure to a patient. A first valve is connected between the fluid reservoir and the upper port, and second valve is connected between the lower port and the patient. During a fill operation, a piston is moved within the syringe to drawn fluid from the reservoir into the syringe through the upper port. During injection operation, the piston moves in an opposite direction to force fluid out of the syringe through the lower port.

26 Claims, 25 Drawing Sheets

U.S. PATENT DOCUMENTS

| | | | |
|---|---|---|---|
| 5,496,559 | 3/1996 | Piechaczek | 604/232 |
| 5,515,851 | 5/1996 | Goldstein . | |
| 5,549,569 | 8/1996 | Lynn et al. . | |
| 5,556,384 | 9/1996 | da Encarnacão . | |
| 5,573,515 | 11/1996 | Wilson et al. . | |
| 5,643,211 | 7/1997 | Sadowski et al. | 604/110 |
| 5,658,252 | 8/1997 | Johnson . | |
| 5,882,343 | 3/1999 | Wilson et al. | 604/246 |

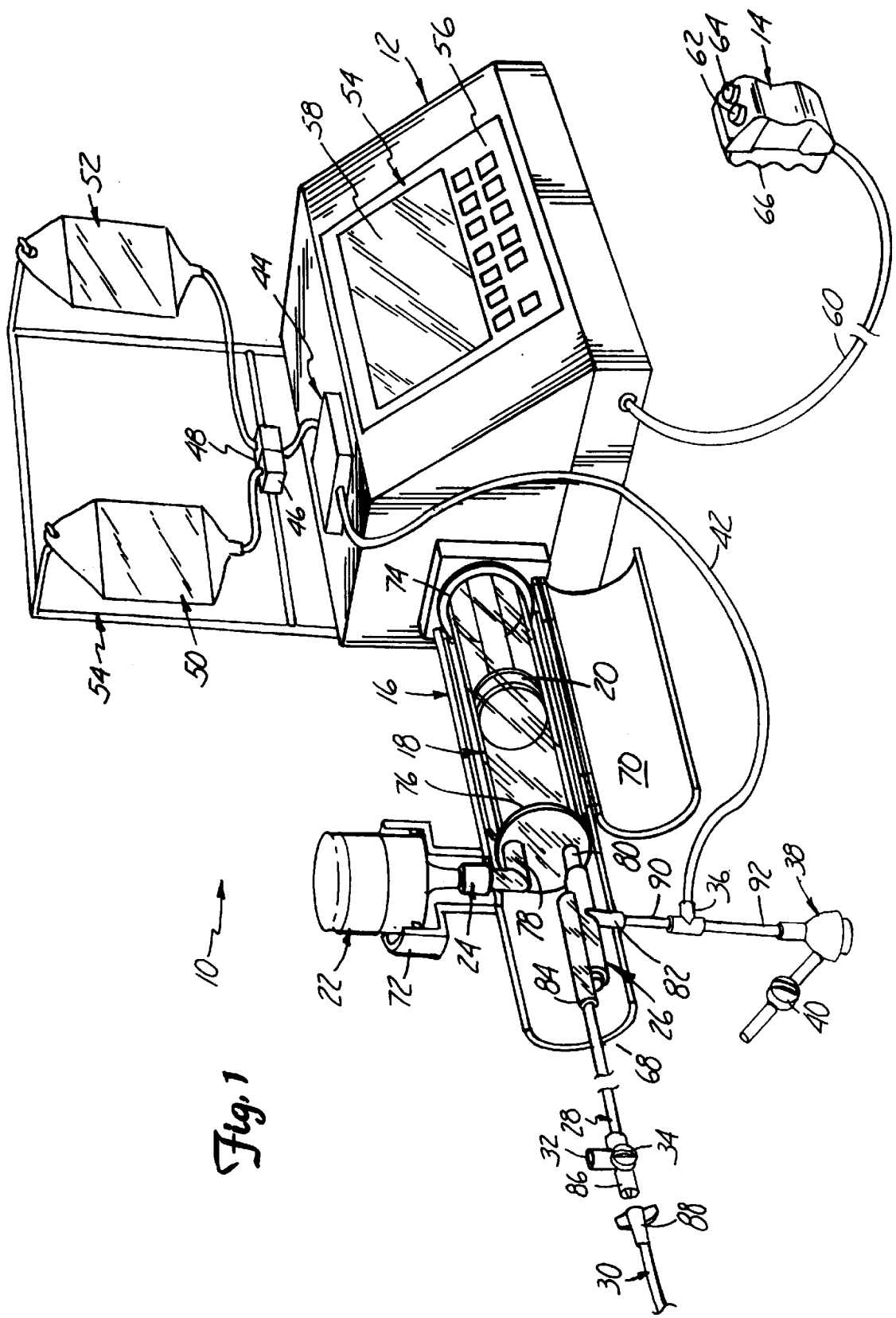

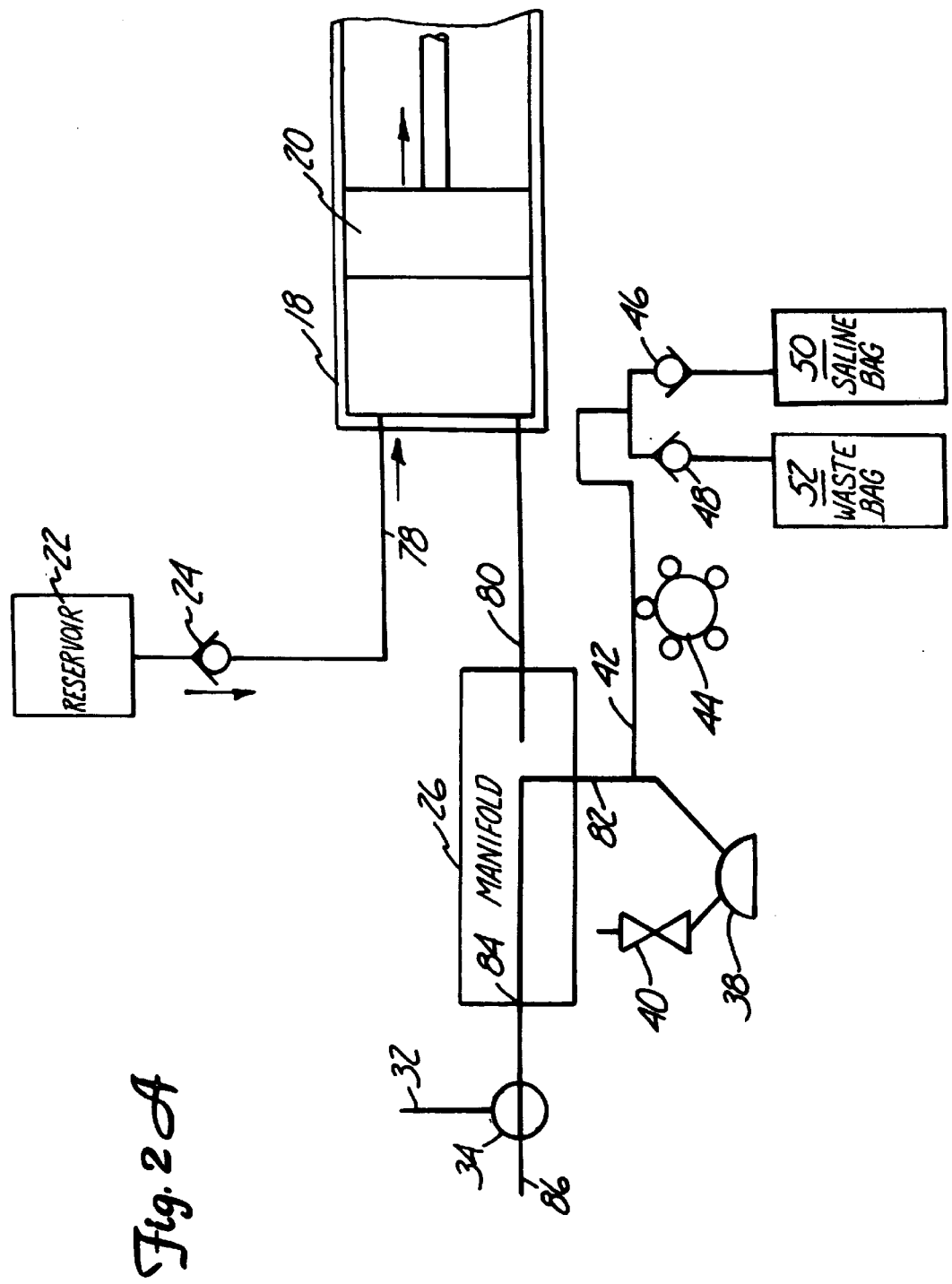

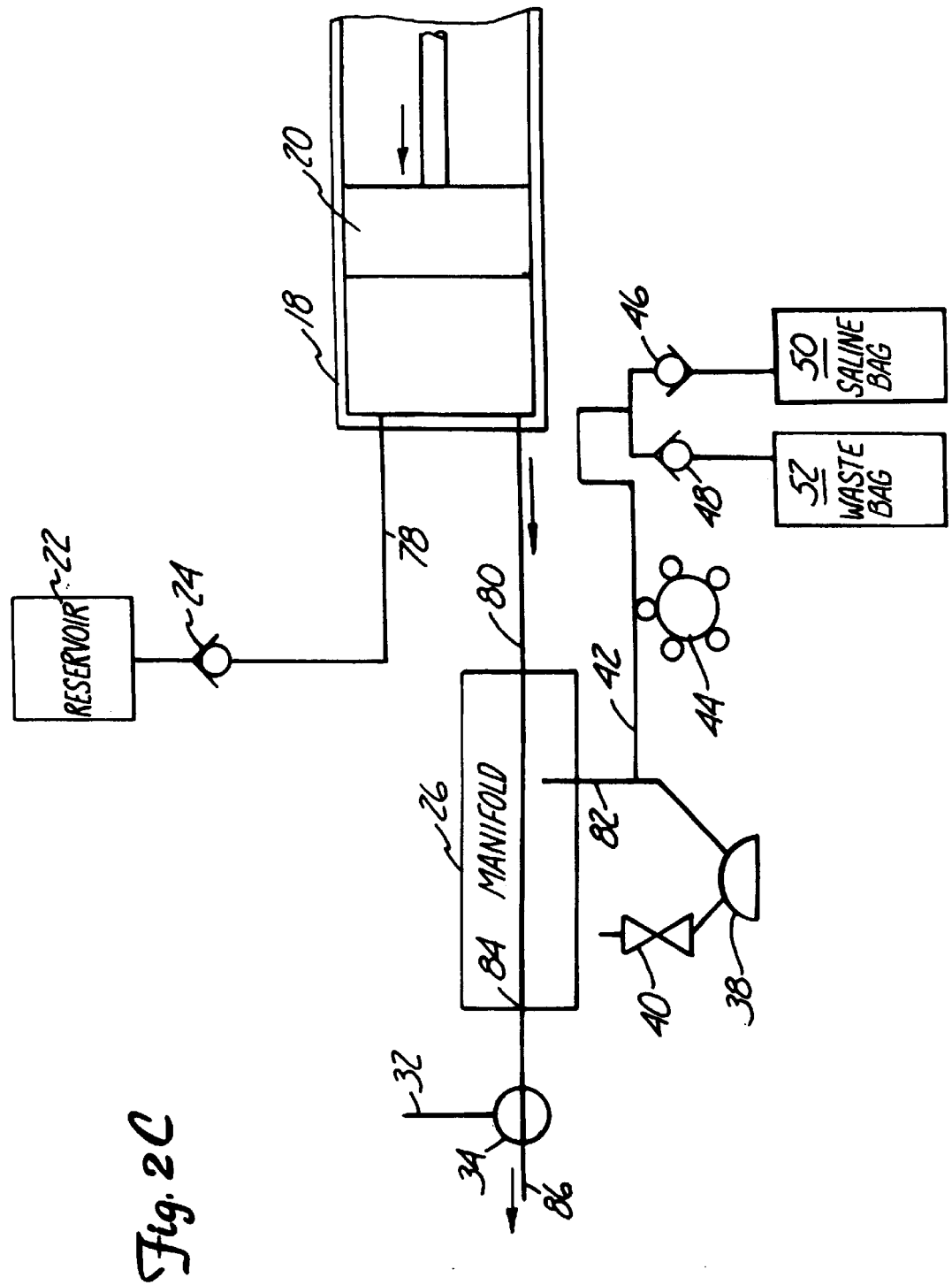

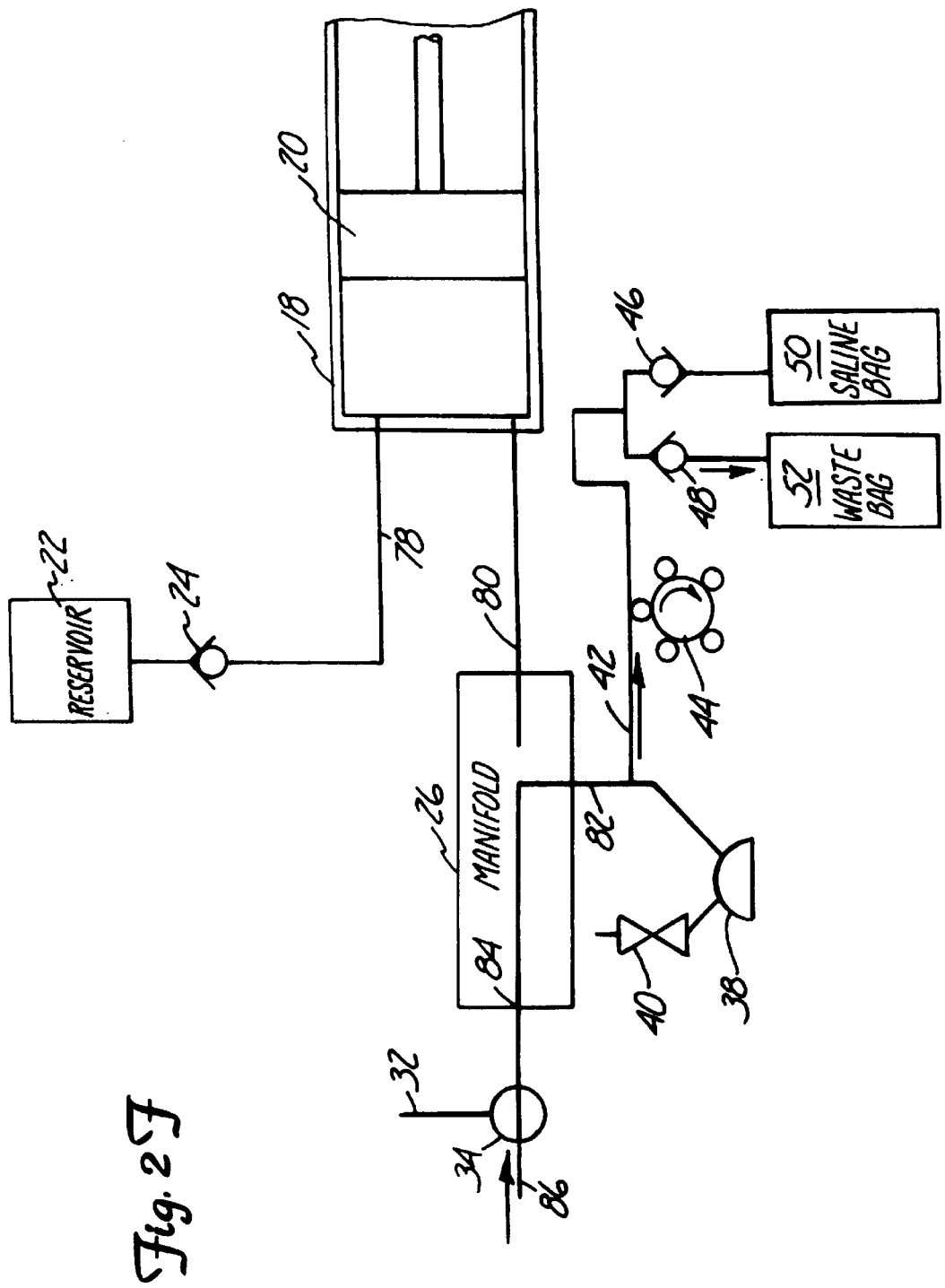

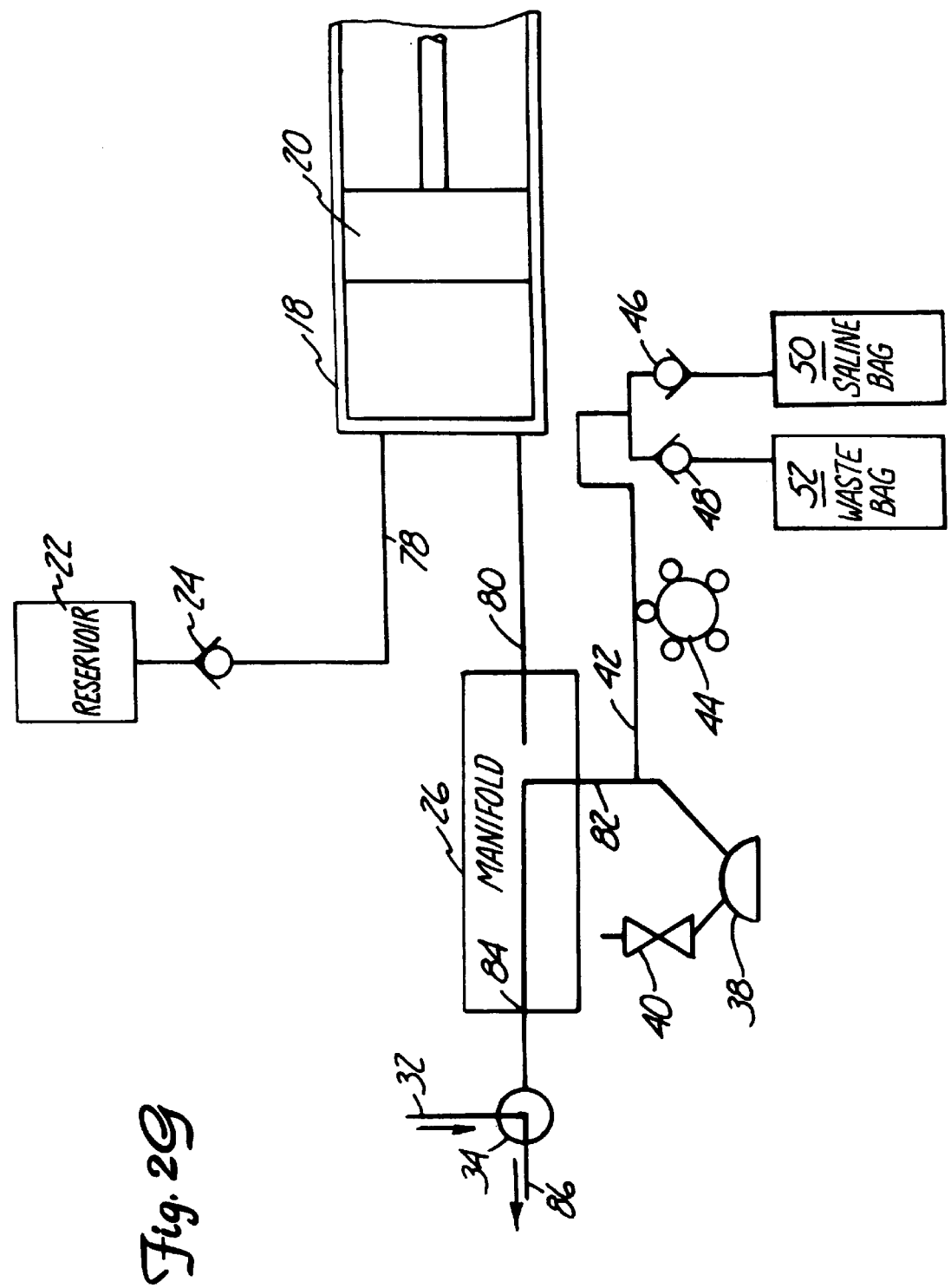

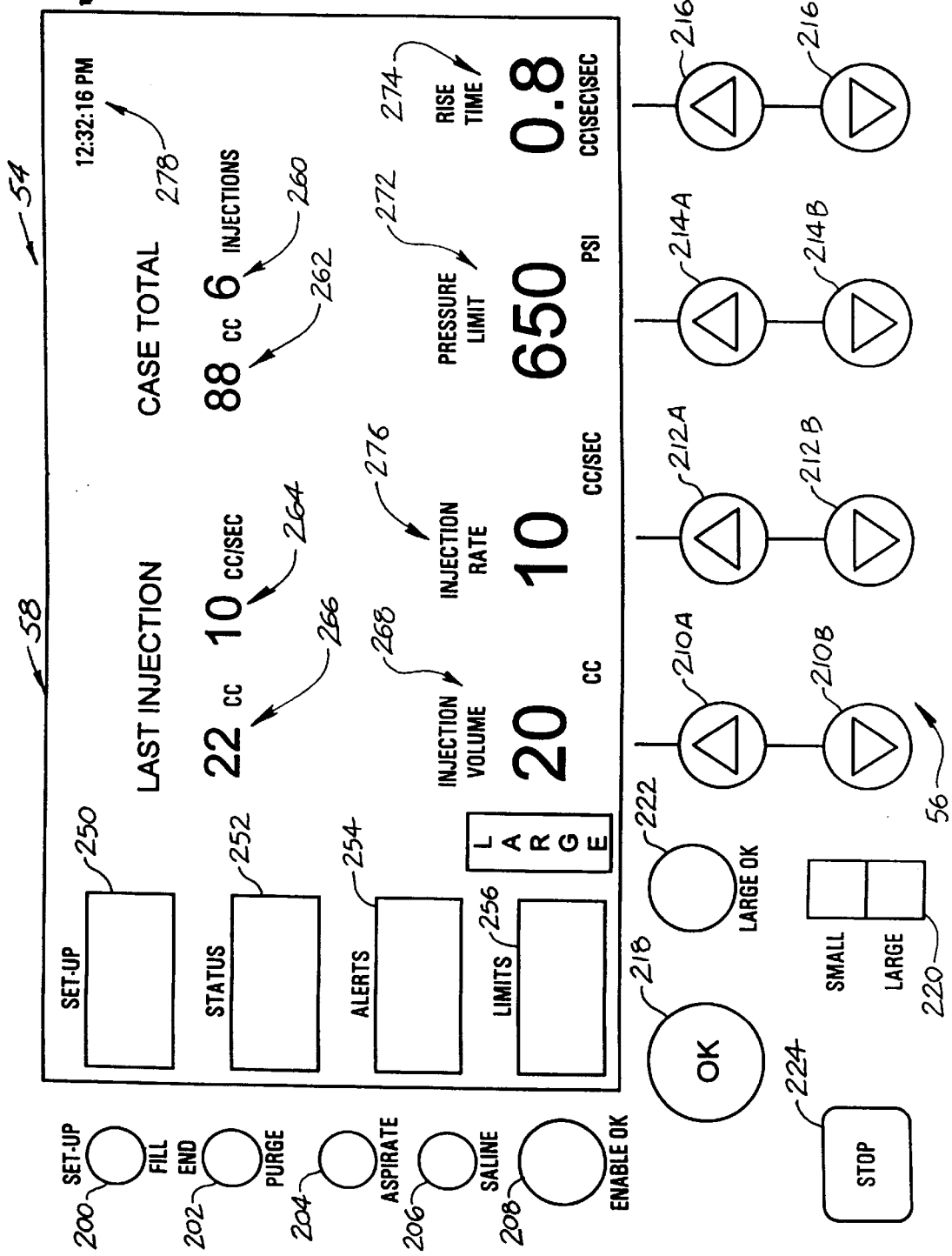

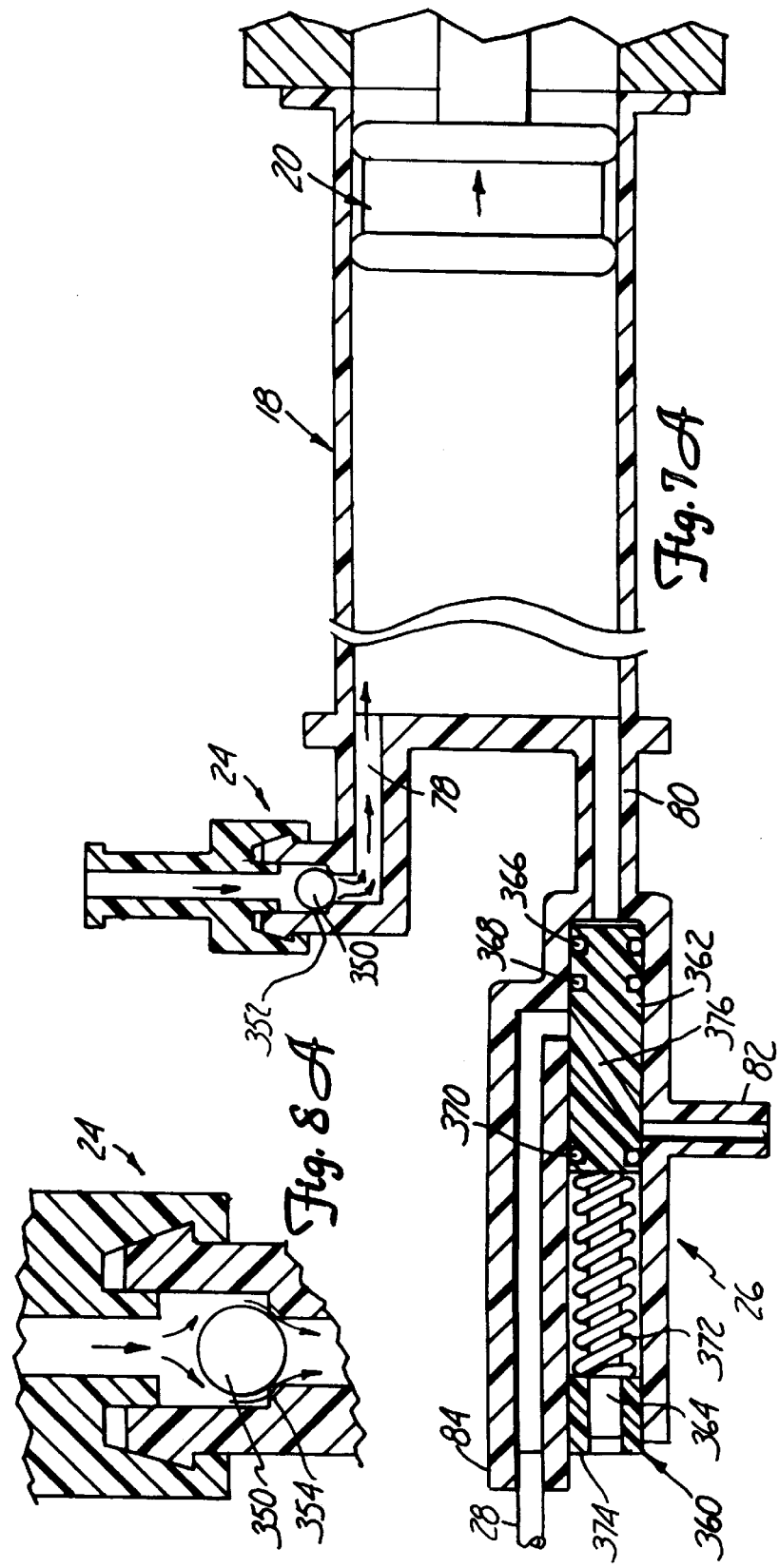

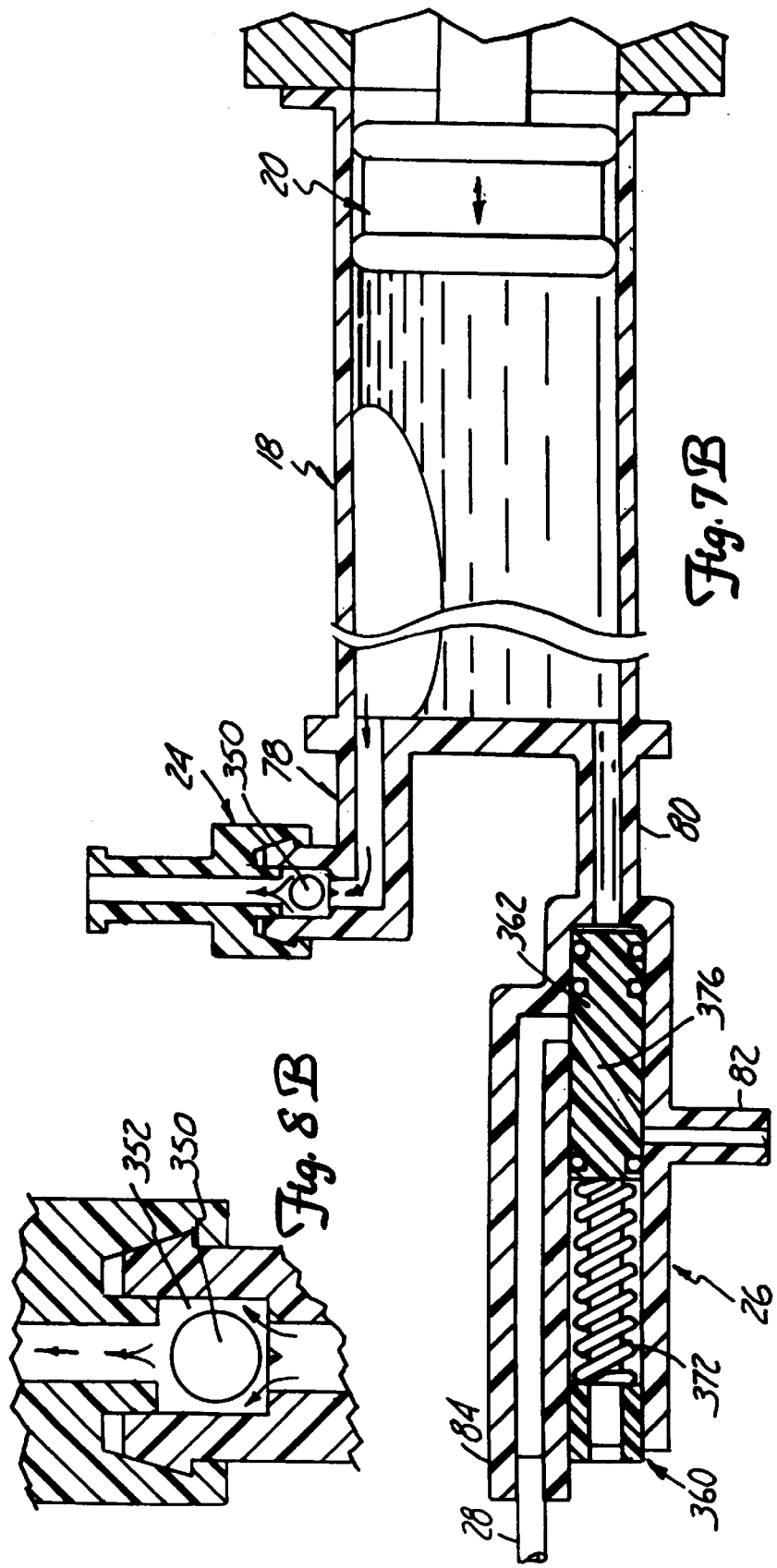

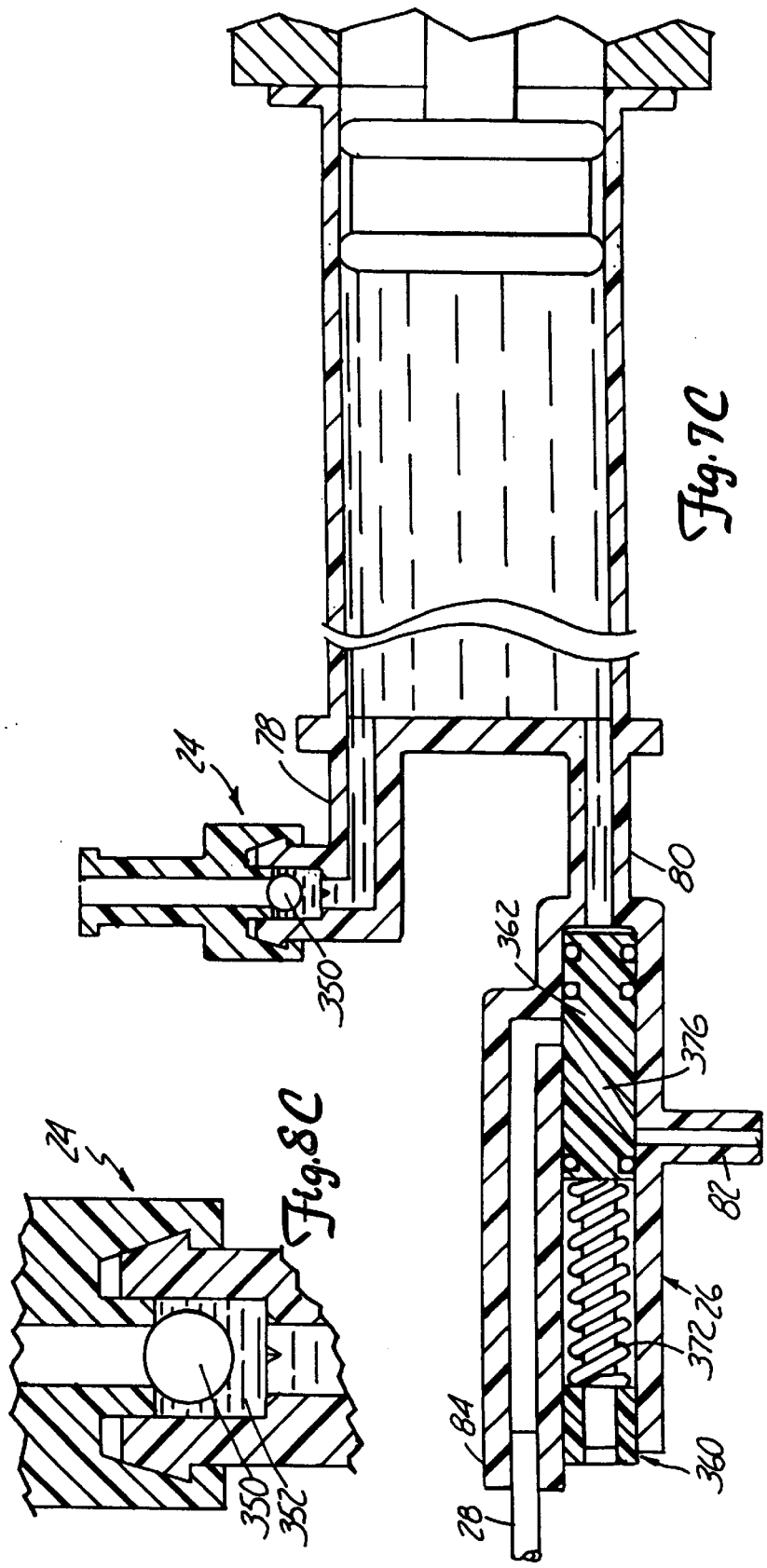

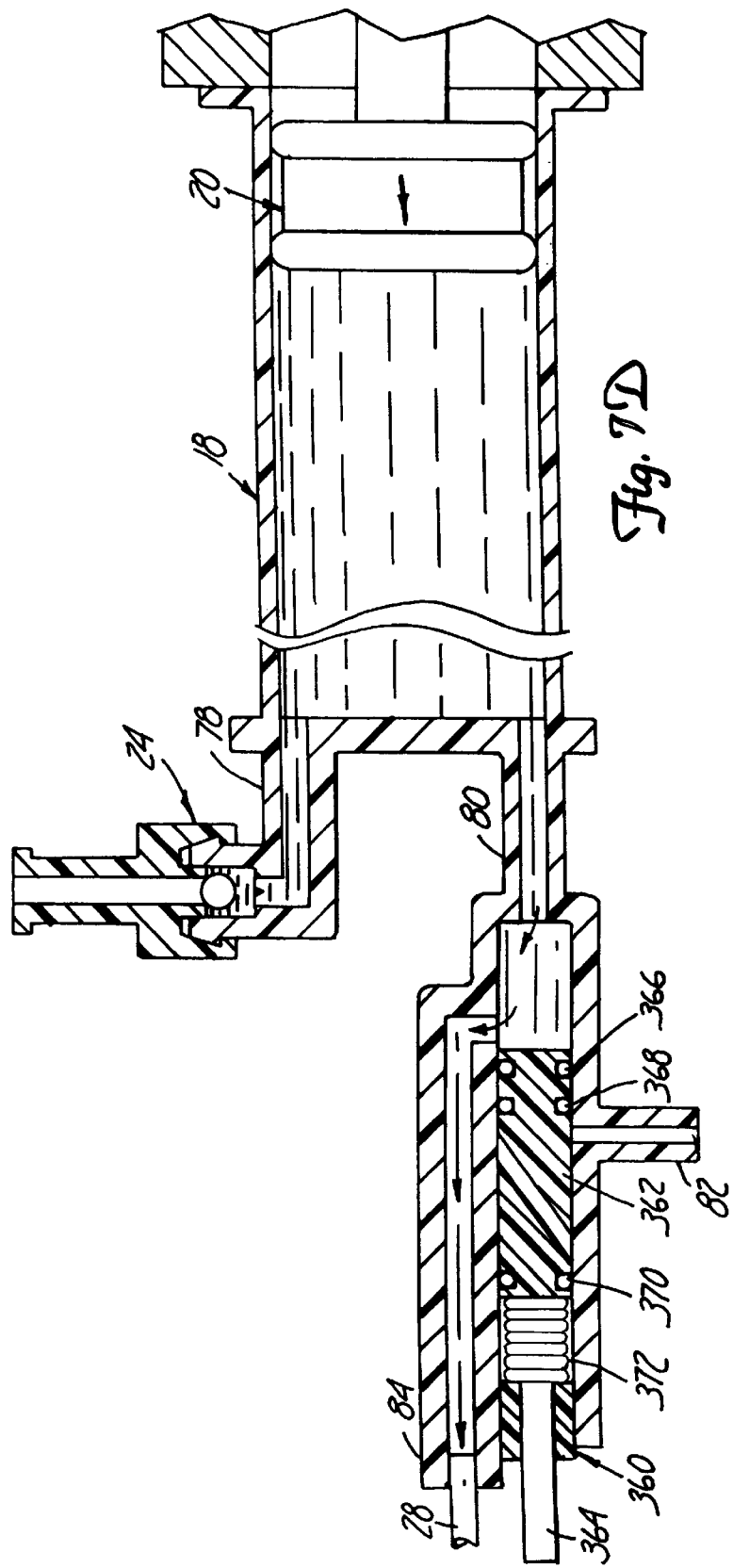

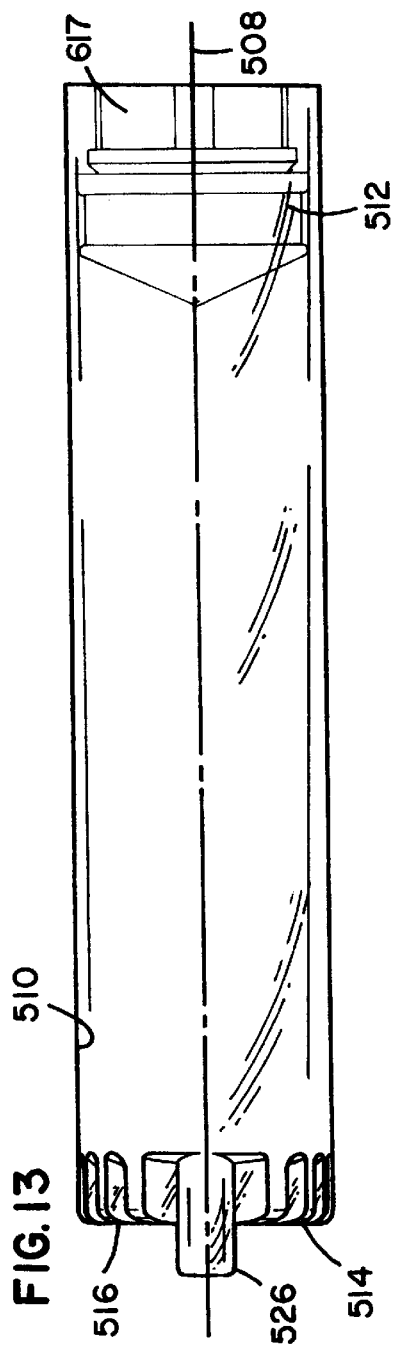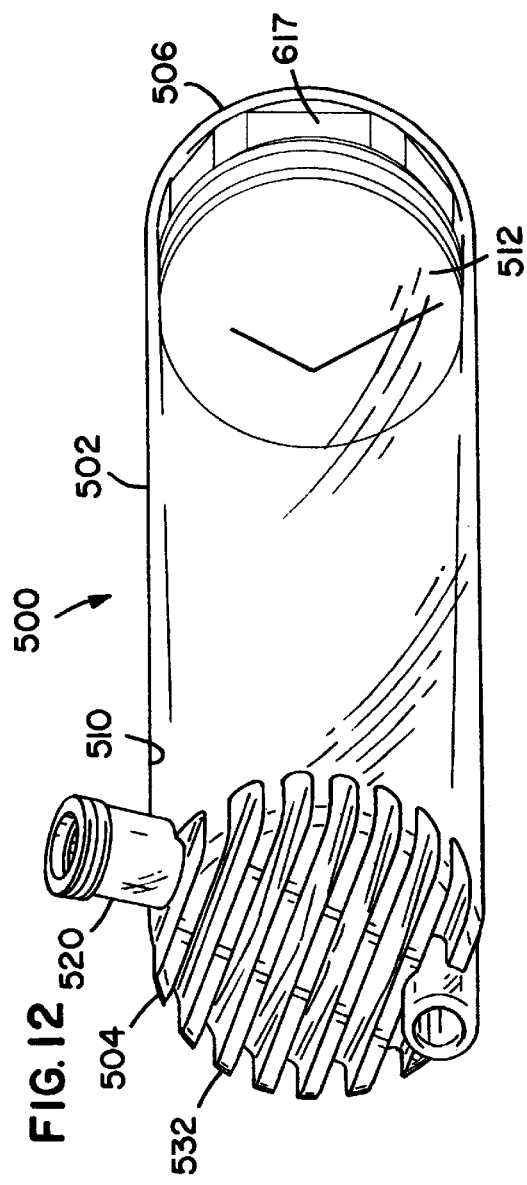

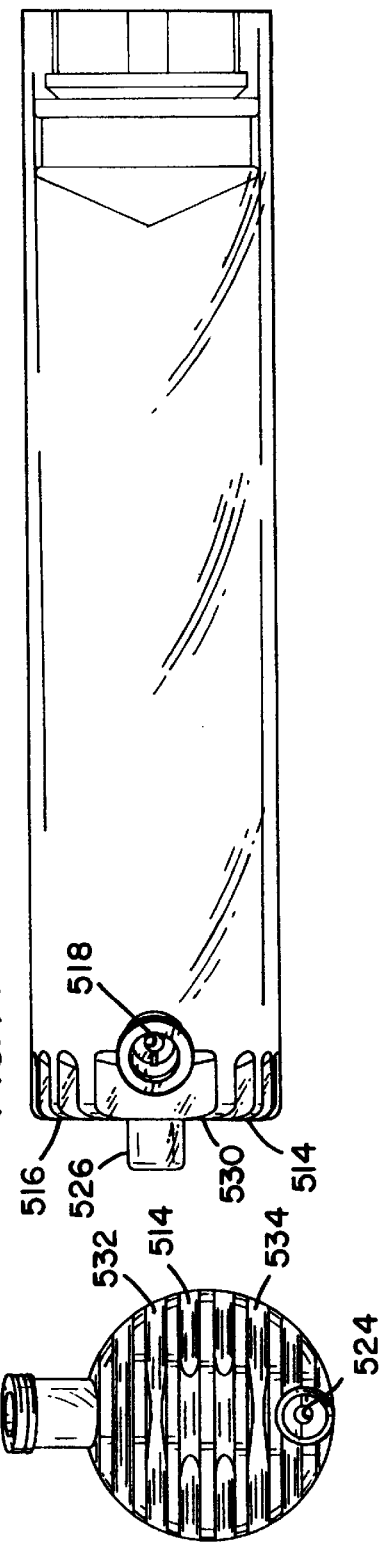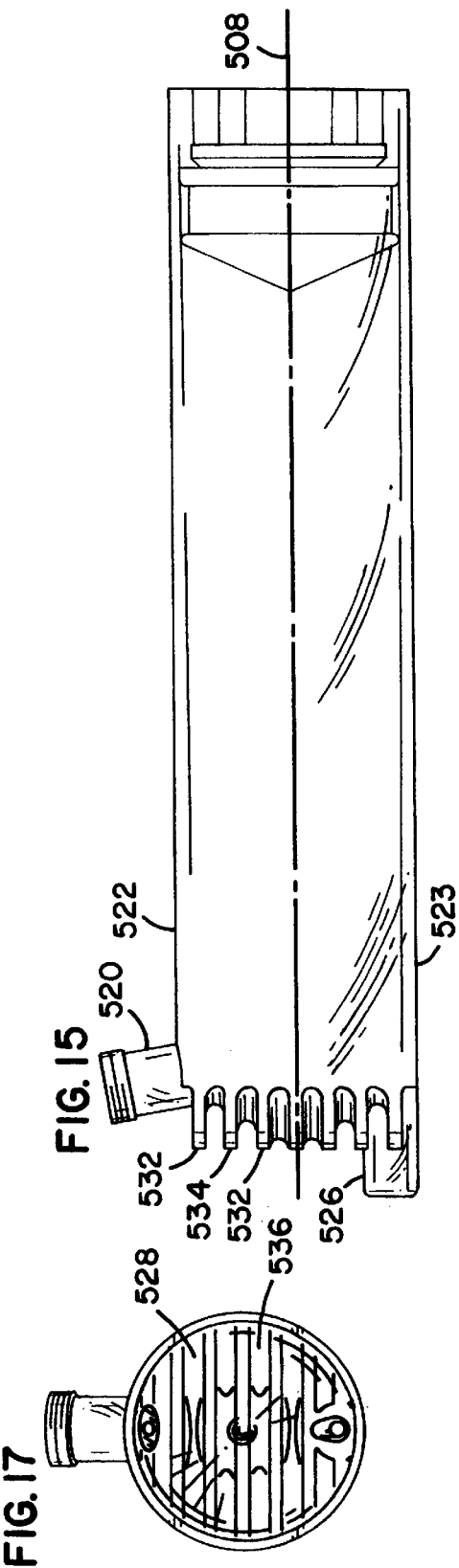

DUAL PORT SYRINGE

This application is a continuation-in-part of Ser. No. 08/946,667, filed Oct. 7, 1997, now U.S. Pat. No. 5,882,343, issued Mar. 16, 1999, which is a continuation of application Ser. No. 08/426,149 filed on Apr. 20, 1995, abandoned. These applications are hereby incorporated by reference.

BACKGROUND OF THE INVENTION

This invention relates to angiography and more specifically, the injector used to inject a medical fluid such as radiographic contrast material into living organisms.

One of the major systems in the human body is the circulatory system. The major components of the circulatory system are the heart, blood vessels, and the blood, all of which are vital to the transportation of materials between the external environment and the different cells and tissues of the human body.

The blood vessels are the network of passageways through which the blood travels in the human body. Specifically, arteries carry the oxygenated blood away from the left ventricle of the heart. These arteries are aligned in progressively decreasing diameter and pressure capability from the aorta, which carries the blood immediately out of the heart to other major arteries, to smaller arteries, to arterioles, and finally to tiny capillaries, which feed the cells and tissues of the human body. Similarly, veins carry the oxygen-depleted blood back to the right atrium of the heart using a progressively increasing diameter network of venules and veins.

If the heart chambers, valves, arteries, veins or other capillaries connected thereto are either abnormal (such as from a birth defect), restricted (such as from atherosclerotic plaque buildup), or deteriorating (such as from aneurysm formation), then a physician may need to examine the heart and connected network of vessels. The physician may also need to correct any problems encountered during the examination with a catheter or similar medical instrument.

Angiography is a procedure used in the detection and treatment of abnormalities or restrictions in blood vessels. During angiography, a radiographic image of a vascular structure is obtained by injecting radiographic contrast material through a catheter into a vein or artery. The vascular structures fluidly connected with the vein or artery in which the injection occurred are filled with contrast material. X-rays are passed through the region of the body in which the contrast, material was injected. The X-rays are absorbed by the contrast material, causing a radiographic outline or image of the blood vessel containing the contrast material. The x-ray images of the blood vessels filled with contrast material are usually recorded onto film or videotape and are displayed on a fluoroscope monitor.

Angiography gives the doctor an image of the vascular structures in question. This image may be used solely for diagnostic purposes, or the image may be used during a procedure such as angioplasty where a balloon is inserted into the vascular system and inflated to open a stenosis caused by atherosclerotic plaque buildup.

Currently, during angiography, after a physician places a catheter into a vein or artery (by direct insertion into the vessel or through a skin puncture site), the angiographic catheter is connected to either a manual or an automatic contrast injection mechanism.

A simple manual contrast injection mechanism typically has a syringe and a catheter connection. The syringe includes a chamber with a plunger therein. Radiographic contrast material is suctioned into the chamber. Any air is removed by actuating the plunger while the catheter connection is facing upward so that any air, which floats on the radiographic contrast material, is ejected from the chamber into the air. The catheter connection is then attached to a catheter that is positioned in a vein or artery in the patient.

The plunger is manually actuated to eject the radiographic contrast material from the chamber, through the catheter, and into a vein or artery. The user of the manual contrast injection mechanism may adjust the rate and volume of injection by altering the manual actuation force applied to the plunger.

Often, more than one type of fluid injection is desired, such as a saline flush followed by the radiographic contrast material. One of the most common manual injection mechanisms used today includes a valve mechanism which controls which of the fluids will flow into the valving mechanism and out to the catheter within the patient. The valve mechanism contains a plurality of manual valves that the user operates manually to open and close that particular fluid channel. When the user suctions or injects contrast fluid into the chamber, the fluid is pulled from the valve mechanism via the open valves. By changing the valve positions, another fluid may be injected.

These manual injection mechanisms are typically hand actuated. This allows user control over the quantity and pressure of the injection. However, all of the manual systems are only capable of injecting the radiographic contrast material at maximum pressure that can be applied by the human hand (i.e., 150 p.s.i). Also, the quantity of radiographic contrast material is typically limited to a maximum of about 12 cc. Finally, there are no safety limits on these manual contrast injection mechanisms which act to restrict or stop injections that are outside of reasonable parameters (such as rate or pressure) and no active sensors to detect air bubbles or other hazards.

Currently used motorized injection devices consist of a syringe connected to a linear actuator. The linear actuator is connected to a motor, which is controlled electronically. The operator enters into the electronic control a fixed volume of contrast material to be injected at a fixed rate of injection. The fixed rate of injection consists of a specified initial rate of flow increase and a final rate of injection until the entire volume of contrast material is injected. There is no interactive control between the operator and machine, except to start or stop the injection. Any change in flow rate must occur by stopping the machine and resetting the parameters.

The lack of ability to vary the rate of injection during the injection results in suboptimal quality of angiographic studies. This is because the optimal flow rate of injections varies considerably between patients. In the cardiovascular system, the rate and volume of contrast injection is dependent on the size of and blood flow rate within the chamber or blood vessel being injected. In many or most cases, these parameters are not known precisely. Moreover, the optimal rate of injection can change rapidly, as the patient's condition changes in response to drugs, illness, or normal physiology. Consequently, the initial injection of contrast material may be insufficient in flow rate to outline the structure on x-ray imaging, necessitating another injection. Conversely, an excessive flow rate might injure the chamber or blood vessel being injected, cause the catheter to be displaced (from the jet of contrast material exiting the catheter tip), or lead to toxic effects from contrast overdose (such as abnormal heart rhythm).

At present, the operator can choose between two systems for injecting contrast material: a manual injection system which allows for a variable, operator interactive flow rate of limited flow rate and a preprogrammed motorized system without operator interactive feedback (other than the operator can start/stop the procedure).

SUMMARY OF THE INVENTION OF APPLICATION SER. NO. 08/426,149

The invention described in 08/426,149 is a dual port syringe used to deliver medical fluids such as angiographic radiographic contrast material to a patient. The dual port syringe includes a syringe body, a piston which is reciprocally movable in the syringe body, and upper and lower parts.

The upper port is connected to a fluid reservoir so that medical fluid is drawn from the fluid reservoir through the upper port into the syringe body when the piston moves in a rearward direction. The lower port is connected to a device, such as a catheter, through which the medical fluid is delivered under pressure to the patient. When the piston moves in a forward direction, medical fluid is delivered under pressure out of the syringe body through the lower port.

In preferred embodiments, the first valve is connected between the fluid reservoir and the upper port, and a second valve is connected between the lower port and patient. The first valve permits flow of fluid from the fluid reservoir to the upper port when the piston moves rearwardly and air to be expelled when the piston moves forwardly. The second valve permits flow of material out of the lower port when the piston moves in a forward direction.

SUMMARY OF THE PRESENT INVENTION

The present invention comprises a syringe for use in a angiographic injector of a type having a syringe holder. The syringe includes a syringe body having a distal end and a proximal end. The syringe body defines a pumping chamber and an inlet port. A syringe end wall is located at the distal end of the syringe body and has a flat face for mating engagement with the syringe holder. The end wall defines an outlet port. A syringe plunger is located in the pumping chamber and is adapted for reciprocal motion between a position proximate to the proximal end and the distal end.

Preferably, the syringe end wall defines an interior portion and an exterior portion. The exterior portion defines the flat face. In preferred embodiments, the exterior portion is reinforced with a plurality of ribs. The ribs each have end portions terminating in a plane transverse to a longitudinal axis of the syringe body. The end portions of the ribs define the flat face. Preferably, the interior portion defines a cone-shaped surface.

In one preferred arrangement, the syringe body defines a top portion. The inlet port is located in the top portion.

Preferably, the end wall defines a first portion and a second portion. The first portion is adjacent to the top portion of the syringe body, and the second portion is adjacent to an end of the end wall opposite of the first portion. The outlet port is preferably located in the second portion of the end wall.

Preferably, a valve arrangement is constructed and arranged to prevent liquid from flowing out of the pumping chamber through the inlet port when the plunger moves from the proximal end to the distal end.

In another aspect, the invention is directed to an injection system comprising a syringe and a syringe holder arrangement. The syringe includes a barrel defining a pumping chamber, a longitudinal axis, and at least one port for providing fluid flow communication with the pumping chamber. The barrel has a distal end and a proximal end. The distal end includes a flat wall section normal to the central longitudinal axis. The syringe includes a plunger constructed and arranged within the pumping chamber for reciprocal motion between a position adjacent to the proximal end and the distal end. The syringe holder arrangement includes a mounting chamber body and door member. The mounting chamber body is constructed and arranged to hold the syringe, and it includes a loading end for receipt of the syringe. The door member is movable relative to the body to allow for selective opening and closing of the loading end of the mounting chamber body. The door member defines a flat, planar surface for abutting engagement with the flat wall section of the syringe.

Preferably, the syringe includes an inlet port and an outlet port. The outlet port is preferably defined by the flat wall section. The syringe includes an inlet port housing surrounding the inlet port, and an outlet port housing surrounding the outlet port. The outlet port housing projects from the flat wall section.

Preferably, the door member defines a slot for slidable communication with the outlet port housing. That is, as the door member rotates into a closed position, the outlet port housing slides in the slot.

In one preferred embodiment, the syringe holder arrangement further includes a pressure containment sleeve selectively mounted within the mounting chamber body for slidable receipt of the syringe. The pressure containment sleeve defines open first and second, opposite ends. The first end is adjacent to the loading end of the mounting chamber body. The door member is selectively movable to open and close the first end.

Preferably, the pressure containment sleeve defines an open channel for slidable communication with the inlet port housing.

In preferred arrangements, the syringe holder arrangement further includes a plate mounted in covering relation to the second end of the pressure containment sleeve. The plate defines an aperture for allowing manipulation of the syringe plunger, when the syringe is positioned in the pressure containment sleeve. Preferably, the syringe holder arrangement further includes a bottle-holder assembly constructed and arranged to mount a bottle in fluid flow communication with the inlet port housing.

In another aspect, the invention is directed to a method for mounting a syringe. The method comprises a step of first, positioning a syringe through a front aperture in a syringe holder arrangement. After the step of positioning a syringe, the method includes pivoting a door of the syringe holder arrangement to close the front aperture and abut a front face of the syringe.

Preferably, the step of positioning a syringe includes providing a syringe having a first end at the syringe front face and defining a fluid port, and a second end slidably receiving a plunger. The step of positioning includes orienting the syringe through the front aperture such that the second end passes through the front aperture followed by the first end.

In one preferred method, the step of positioning a syringe includes inserting the syringe into an interior of a pressure containment sleeve.

Preferably, the front face of the syringe is planar with an outlet port housing extending therefrom surrounding the fluid port, and the door includes a planar surface. The step of pivoting a door includes sliding the planar surface of the door relative to the planar, front face of the syringe.

It is to be understood that both the foregoing general description and the following detailed description are exemplary and explanatory only and are not restrictive of the invention, as claimed.

BRIEF DESCRIPTION OF THE DRAWINGS

FIG. 1 is a perspective view illustrating a preferred embodiment of the angiographic injector system of the present invention.

FIGS. 2A–2G are diagrams illustrating operations of the system of FIG. 1.

FIG. 4 illustrates front panel controls and displays of a preferred embodiment of the injector system of the present invention.

FIGS. 7A–7D illustrate the operation of the inlet check valve and manifold during contrast fill, air purge, and patient inject operations.

FIGS. 8A–8C illustrate operation of the inlet check valve in greater detail.

FIG. 12 is a perspective view of one embodiment of a syringe usable in the angiographic injector system, according to the present invention.

FIG. 13 is a bottom plan view of the syringe depicted in FIG. 12.

FIG. 14 is a top plan view of the syringe depicted in FIG. 12.

FIG. 15 is a side elevational view of the syringe depicted in FIG. 12.

FIG. 16 is a front side elevational view of the syringe depicted in FIG. 12.

FIG. 17 is a rear side elevational view of the syringe depicted in FIG. 12, and without the plunger therein.

DETAILED DESCRIPTION OF THE PREFERRED EMBODIMENTS

A. Application Ser. No. 08/426,149

Figure 2B:
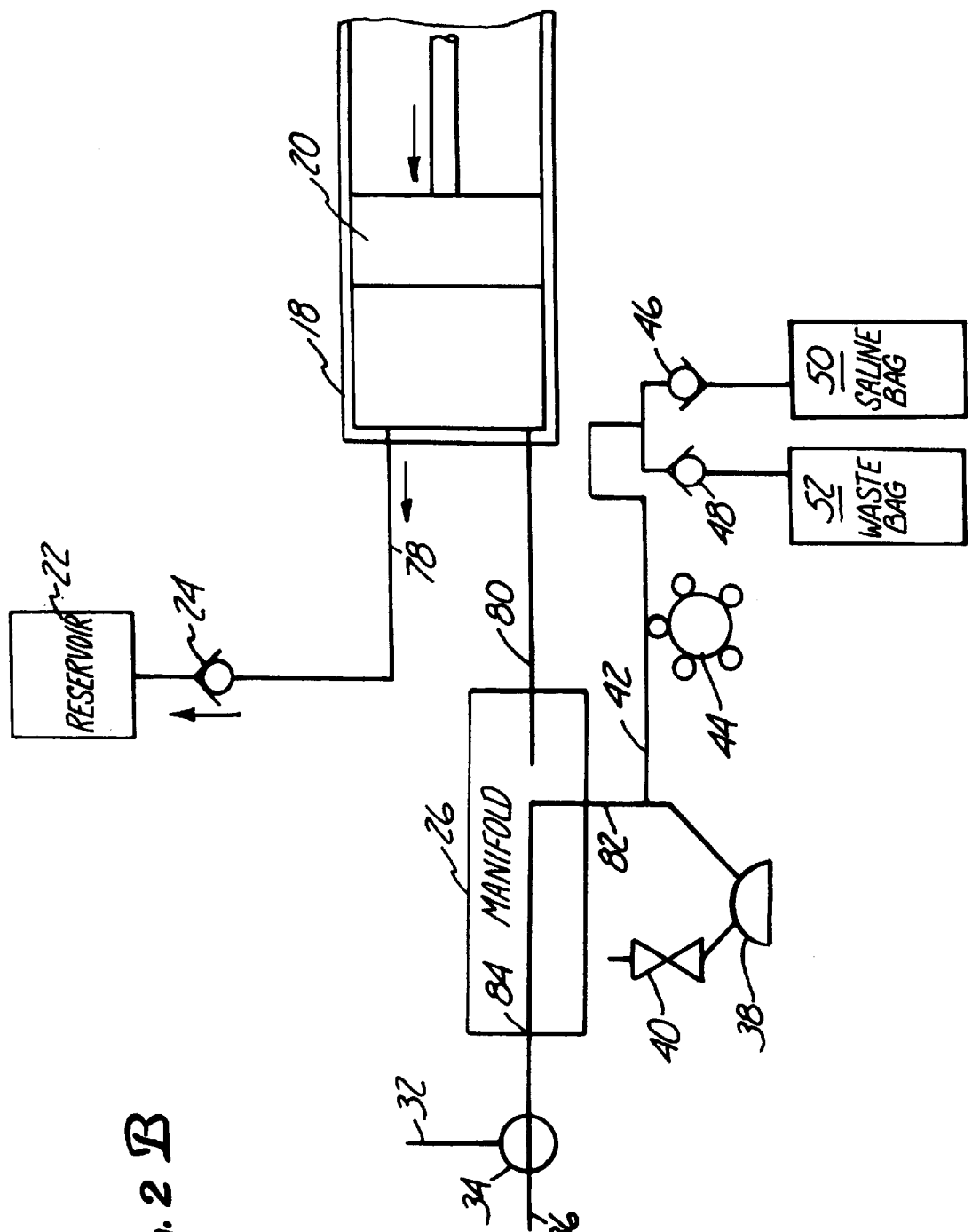

FIG. 1 shows angiographic injector system 10 for injecting radiographic contrast material into a blood vessel under interactive physician control. System 10 includes main console 12, hand held remote control 14, syringe holder 16, syringe body 18, syringe plunger 20, radiographic material reservoir (bottle) 22, one-way valve 24, manifold 26, high pressure tube 28, catheter 30, patient medication port 32, three-way stop-cock 34, T-connector 36, pressure transducer 38, stop-cock 40, tubing 42, peristaltic pump 44, saline check valve 46, waste check valve 48, saline bag 50, waste bag 52, and bag support rack 54.

Console 12 houses the electrical controls for system 10, together with the motors which drive piston 20 and peristaltic pump 44. On the front surface of console 12, user interface 54 provides control switches 56 and display 58 through which the user may enter control settings and monitor the operational state of system 10.

Remote control 14 is connected to console 12 by cable 60 (although in other embodiments remote control 14 may be connected by a wireless connection such as an RF, infrared optic, or ultrasonic link). Remote control 14 is, in the embodiment shown in FIG. 1, a hand-held control which includes reset and saline push button switches 62 and 64, respectively, and flow rate control lever or trigger 66. By squeezing trigger 66, the user can provide a command signal to console 12 to provide a continuously variable injection rate.

Syringe holder 16 projects from the left hand side of console 12. Syringe holder 16 is preferably a clear material, and includes a half cylindrical back shell 68, a half cylindrical front door 70 (which is shown in open position in FIG. 1), and reservoir holder 72.

Syringe 18 is a transparent or translucent plastic cylinder having its open end 74 connected to console 12. Closed end 76 of syringe 18 contains two ports: upper port 78 and lower port 80.

Plunger 20 is movable within syringe body 18. Plunger 20 is connected to, and driven by a motor located within console 12.

Radiographic contrast material reservoir 22 is connected through one-way check valve 24 to upper port 78. Radiographic contrast material is drawn from reservoir 22 through check valve 24 and upper port 78 into the pumping chamber defined by syringe body 18 and plunger 20. Check valve 24 is preferably a weighted one-way valve which permits air to flow from syringe body 18 back into reservoir 22, but will not permit radiographic contrast material to flow from syringe body 18 to reservoir 22. This permits automatic purging of air from the system, as will be described in more detail later.

Lower port 80 of syringe body 18 is connected to manifold 26. Manifold 26 includes a spring biased spool valve which normally connects transducer/saline port 82 and patient port 84. When radiographic contrast material is to be injected, the pressure of the radiographic material causes the spool valve to change states so that lower port 80 is connected to patient port 84.

High pressure tube 28 is a flexible tube which connects patient port 84 to catheter 30. Three-way stop-cock 34 is located at the distal end of tube 28. Rotatable luer lock connector 86 is connected to stop-cock 34 and mates with luer connector 88 at the proximal end of catheter 30. Stopcock 34 either blocks flow between tube 28 and catheter 30, permits flow, or connects medication port 32 to catheter 30.

In addition to injecting radiographic material into a patient through catheter 30, system 10 also permits other related functions to be performed. A device for delivering the patient medication (not shown in FIG. 1) may be connected to medication port 32 when medication is to be delivered through catheter 30 to the patient.

When catheter 30 is in place in the patient, and an injection of radiographic contrast material is not taking place, pressure transducer 38 monitors the blood pressure through the column of fluid which extends from catheter 30, tube 28, patient port 84, manifold 26, transducer/saline port 82, tubing 90, T-connector 36, and tubing 92. Transducer 38 has an associated stop-cock 40 which allows transducer 38 to be exposed to atmospheric pressure during calibration and also allows for removal/expulsion of trapped air so the dome chamber of transducer 38 can be flushed with saline.

Peristaltic pump 44 supplies saline solution from bag 50 through saline check valve 46, tubing 42, T-connector 36 and tubing 90 to saline port 82. When peristaltic pump 44 is operating to supply saline solution, the saline solution is supplied through manifold 26 to patient port 84 and then through tube 28 to catheter 30.

Peristaltic pump 44 also operates in an opposite direction to draw fluid from catheter 30 and through tube 28, manifold 26, tubing 90, T-connector 36 and tubing 42 to waste check valve 48 and then into waste collection bag 52.

In a preferred embodiment of the invention, syringe body 18, manifold 26, tube 28, catheter 30, T-connector 36, tubing 42, check valves 46 and 48, bags 50 and 52, and tubing 90 and 92 are all disposable items. They must be installed in system 10 each time an angiography procedure is to be performed with a new patient. Once system 10 is set up with all the disposable items installed, door 70 is closed, and syringe body 18 filled with contrast material and purged of air, the user (typically a physician) enters into system 10 the safety parameters that will apply to the injection of radiographic contrast material. These safety parameters typically include the maximum amount of radiographic contrast material to be injected during any one injection, the maximum flow rate of the injection, the maximum pressure developed within syringe body 18, and the maximum rise time or acceleration of the injection. To actuate an injection of contrast material, the user operates remote control 14 by squeezing trigger 66. Within the preset safety parameters, system 10 causes the flow rate of the injection to increase as the force or distance of travel of trigger 66 is increased.

Typically, the user will meter the amount and rate of contrast material injected based upon continuous observation of the contrast outflow into the structure being injected using fluoroscopy or other imaging methods. System 10 allows the user to tailor the contrast injections to the needs of the patient, thereby maximizing the quality of the procedure, increasing the safety, and reducing the amount of contrast material required to perform the fluoroscopic examination.

FIGS. 2A–2G are diagrams illustrating fluid flow paths during seven different operations of system 10. Those operations are contrast fill (FIG. 2A), air purge (FIG. 2B), patient inject (FIG. 2C), patient pressure (FIG. 2D), saline flush (FIG. 2E), aspirate waste (FIG. 2F), and medicate patient (FIG. 2G).

The contrast fill operation illustrated in FIG. 2A involves the filling of syringe body 18 with radiographic contrast material from reservoir (contrast media supply) 22. The contrast fill operation is performed during initial set up of system 10, and may be repeated during operation of system 10 whenever syringe body 18 is running low on radiographic contrast material.

During initial set up of system 10, plunger 20 is initially driven to its furthest forward position adjacent closed end 76 of syringe body 18. This will expel to the atmosphere the majority of the air which is located within syringe body 18.

Plunger 20 is then retracted, which creates a vacuum within syringe body 18 which draws contrast material from reservoir 22 through check valve 24 into syringe body 18 through upper port 78.

The Contrast Fill operation typically will result in some air being drawn into or remaining within syringe body 18. It is important, of course, to prevent air from being injected into the patient through catheter 30. That is the purpose of the Air Purge operation shown in FIG. 2B. Also, the location of two ports at different elevations allows for a greater amount of safety in preventing air bubbles in the injection.

During the Air Purge operation, plunger 20 travels forward to expel trapped air within syringe body 18. The air, being lighter than the contrast material, gathers near the top of syringe body 18. As plunger 20 moves forward, the air is expelled from syringe body 18 through upper port 78 and one-way valve 24. In the embodiment illustrated in FIG. 2B, one-way valve 24 is a weighted one-way valve which allows flow of radiographic contrast material from reservoir 22 to upper port 78, but will not allow radiographic contrast material to flow in the opposite direction from upper port 78 to reservoir 22. Valve 24 will, however, allow air to flow from port 78 to reservoir 22. As soon as radiographic contrast material begins flowing out of syringe body 18 through upper port 78 to valve 24, valve 24 closes to prevent any further flow toward reservoir 22.

Valve 24 can also, in alternative embodiments, can be a solenoid actuated or motor driven valve operated under control of the electric circuitry within console 12. In either case, valve 24 is capable to withstanding the relatively high pressures to which it will be subjected during the inject operation. Preferably, valve 24 is capable of withstanding static fluid pressures up to about 1200 p.s.i.

FIG. 2C illustrates the Patient Inject operation. Plunger 20 travels forward under the interactive control of the user, who is controlling trigger 66 of remote control 14. The movement of plunger 20 creates hydraulic pressure to force contrast material out of syringe body 18 through lower port 80 and through manifold 26 and high pressure tube 28 into catheter 30. As shown in FIG. 2C, syringe lower port 80 and patient port 84 are connected for fluid flow during the patient inject operation.

Manifold 26 contains a valve which controls the routing of fluid connections between patient port 84 and either syringe bottom port 80 or transducer/saline port 82. In one embodiment of the invention, manifold 26 includes a spool valve which is spring biased so that patient port 84 is normally connected to transducer/saline port 82 (as illustrated in FIGS. 2A and 2B). When the pressure at syringe bottom port 80 builds with the movement of plunger 20 forward, the bias force against the spool valve is overcome so that syringe bottom port 80 is connected to patient port 84, and transducer/saline port 82 is disconnected the valve within manifold 26 protects pressure transducer 38 from being exposed to the high pressure generated by the patient inject operation.

The spool valve opens automatically during the patient inject operation in response to increase pressure exerted on it from the syringe lower port 80. The spool valve closes and returns to its original position allowing for connection of patient port 84 to transducer 38 when a slight vacuum is applied by retraction of plunger 20 at the end of each Patient Inject operation.

In an alternative embodiment, the valve within manifold 26 is an electromechanical or motor driven valve which is actuated at appropriate times to connect either syringe lower port 80 or transducer/saline port 82 to patient port 84. The actuator mechanism is controlled by console 12. Once again in this alternative embodiment, the valve protects pressure transducer 38 from being exposed to high pressure.

Figure 2D:
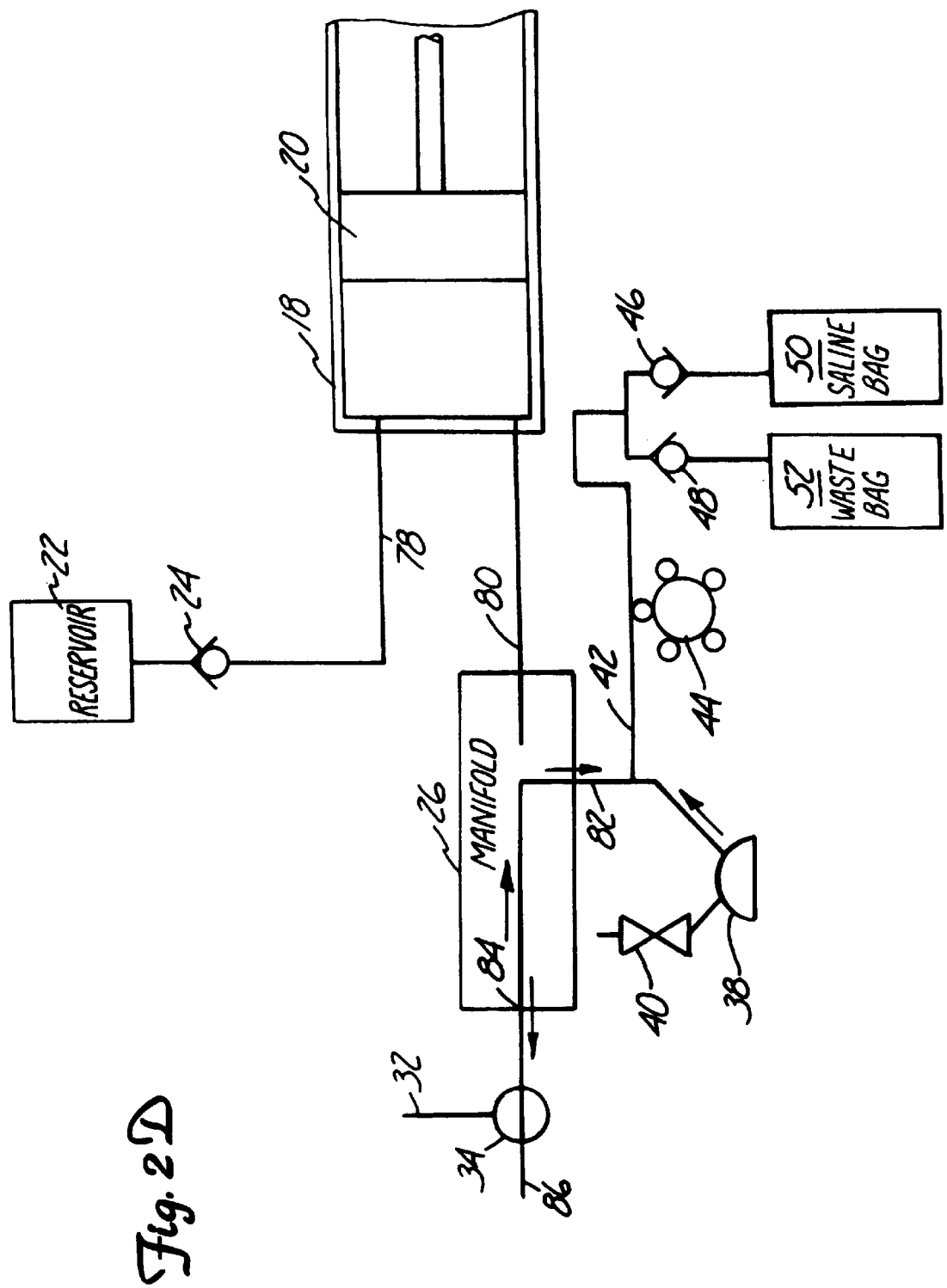

FIG. 2D illustrates the Patient Pressure operation. System 10 allows for reading of the patient's blood pressure, which is monitored through catheter 30. Patient blood pressure can be monitored through the use of pressure transducer 38 at any time except during the patient inject, saline flush, and waste aspirate operations. The pressure reading being produced by pressure transducer 38 may be normalized by manually opening stop-cock 40 and closing stop-cock 34 to expose pressure transducer 38 to atmospheric pressure.

Figure 2E:
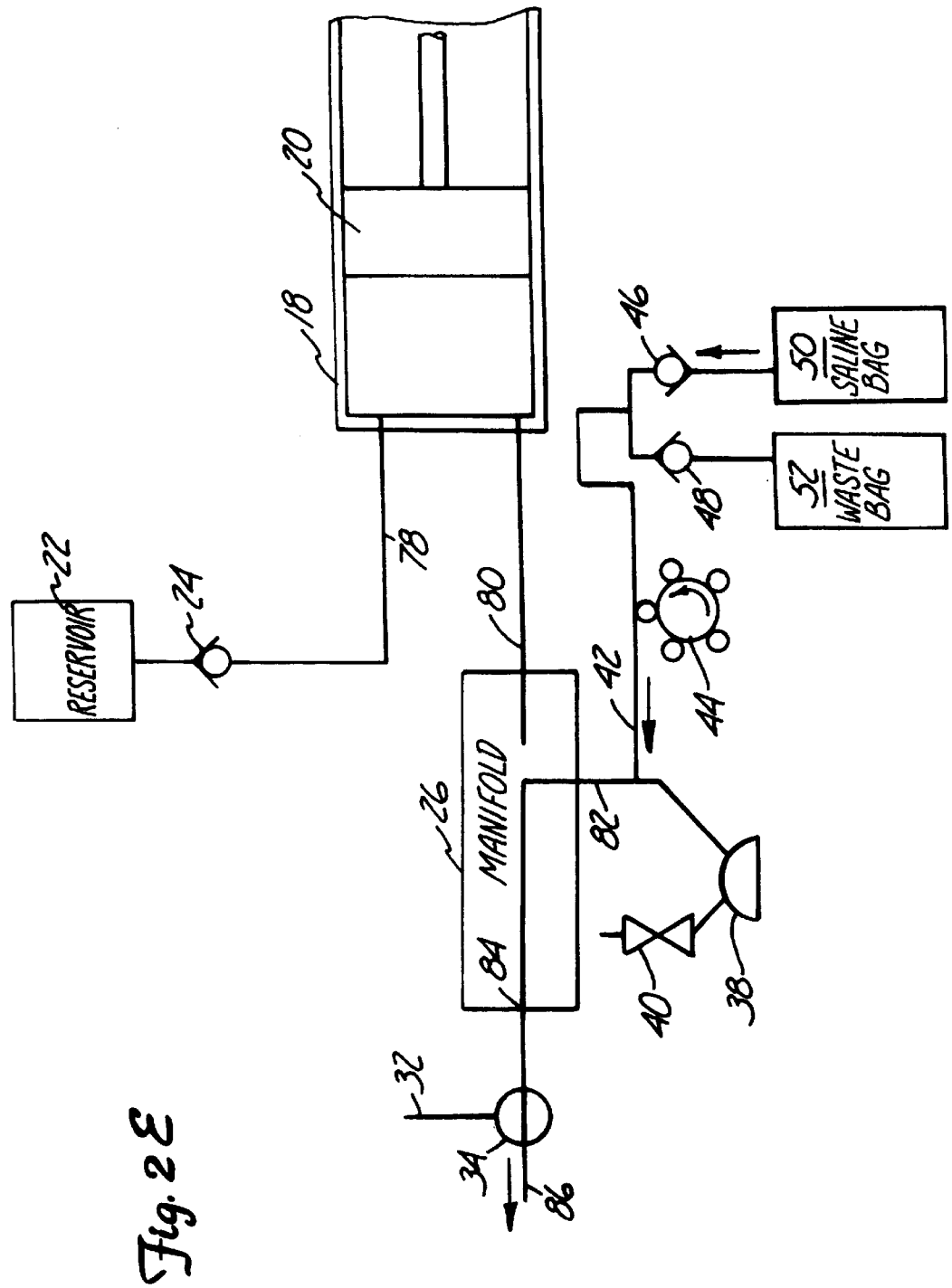

During the Saline Flush operation illustrated in FIG. 2E, saline solution is used to flush all of the internal lines, pressure transducer chamber 38, tube 28, and catheter 30. As shown in FIG. 2E, peristaltic pump 44 is operating in a direction which causes saline solution to be drawn from bag 50 through check valve 46 and through tubing 42 to saline port 82. Manifold 26 connects saline port 82 to patient port 84 so that saline solution is pumped out of patient port 84 and through tube 28 and catheter 30.

During the Aspirate Waste operation, patient port 84 is again connected to saline port 82. During this operation, peristaltic pump 44 is operating in the opposite direction from its rotation during the saline flush operation. As a result, patient fluids are aspirated from patient port 84 to saline port 82 and then through tubing 42 and check valve 48 into waste collection bag 52. Peristaltic pump 44 acts as a valve pinching/occluding tubing 42 and preventing back flow to/from saline and waste containers 50 and 52 in conjunction with check valves 46 and 48.

With catheter 30 in place within the patient, it may be desirable to supply patient medication. System 10 allows for that option by providing patient medication port 32. As shown in FIG. 2G, when stop-cock 34 is open, a medication source connected to port 32 will be connected to patient port 84, and thereby to catheter 30. During the medicate patient operation, peristaltic pump 44 and plunger 20 are not moving.

Figure 3A:
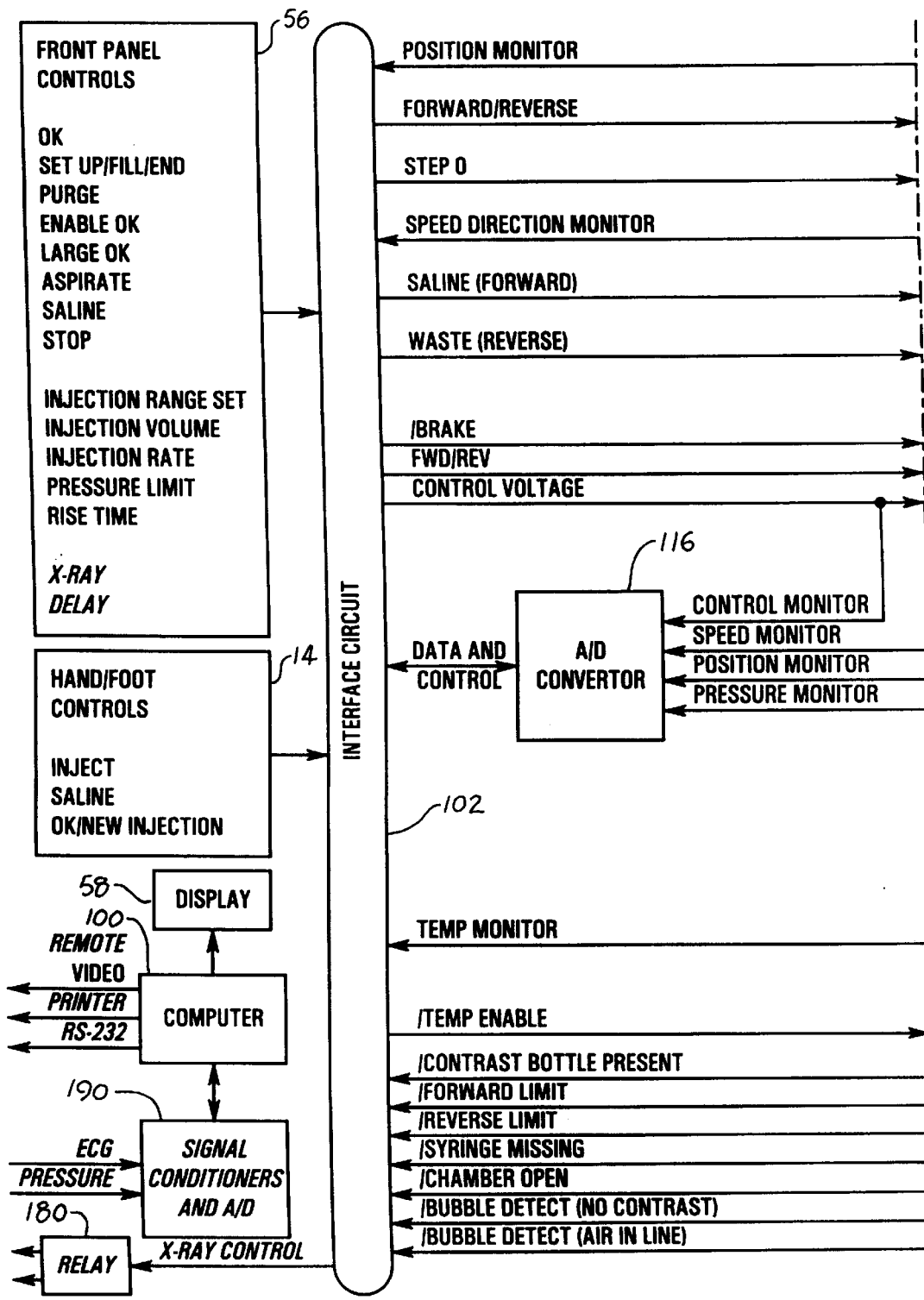
FIGS. 3A and 3B are electrical block diagrams of the control system of the injector system of FIG. 1.
Figure 3B:
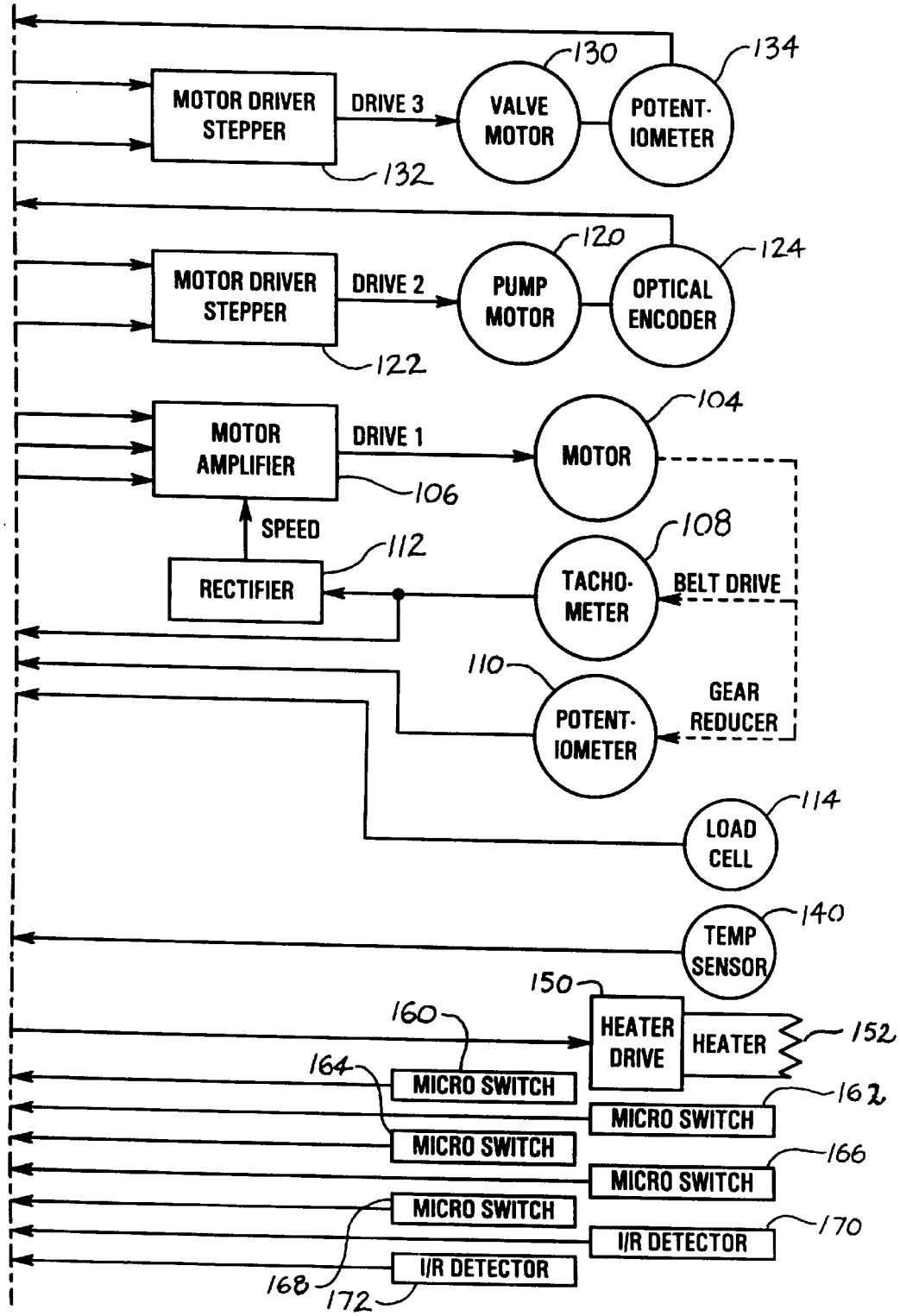

FIG. 3 is an electrical block diagram of the control system which controls the operation of angiographic injector system 10. The electrical control system includes digital computer 100, which receives input signals from remote control 14 and front panel controls 56 through interface 102, and provides signals to display 58 to display operation data, alerts, status information and operator prompts.

Computer 100 controls the motion of plunger 20 through a motor drive circuit which includes motor 104, motor amplifier 106, tachometer 108, potentiometer 110, a rectifier 112, pressure sensing load cell 114, and A/D converter 116.

Motor amplifier 106 provides a drive signal to motor 104 in response to Control Voltage, Fwd/Rev, and/Brake signals from computer 100 and a speed feedback signal from tachometer 108 through rectifier 112. The outputs of tachometer 108 and potentiometer 110 are supplied to computer 100 through A/D converter 116 as Speed Monitor and Position Monitor signals. These allow computer 100 to check motor speed, motor direction, and position (volume is a calculated value).

Pressure sensor 114 senses motor current or plunger force in order to measure the pressure being applied to the radiographic contrast material within syringe body 18. This Pressure Monitor Signal is supplied through A/D converter 116 and interface 102 to computer 100.

Peristaltic pump 44 is driven under the control of computer 100 through pump motor 120, motor driver 122 and optical encoder 124. Computer 100 provides Saline (Forward) and Waste (Reverse) drive signals to motor driver 122 to operate pump motor 120 in a forward direction for saline flush and a reverse direction for waste aspiration. Optical encoder 124 provides the Speed Direction Monitor signal to interface 102 which indicates both the speed and the direction of rotation of pump motor 120.

FIG. 3 illustrates an embodiment of the control system in which valve motor 130 is used to actuate valves such as one-way valve 24 and the valve within manifold 26. In this embodiment, computer 100 controls valve motor 130 through motor driver 132, and monitors position through a Position Monitor feedback signal from potentiometer 134. In this particular embodiment, valve motor 130 is a stepper motor.

Computer 100 monitors temperature of the contrast material based upon a Temp Monitor signal from temperature sensor 140. Temperature sensor 140 is preferably positioned near syringe body 18. If the temperature being sensed by temperature sensor 140 is too high, computer 100 will disable operation motor 104 to discontinue patient injection. If the temperature is too low, computer 100 provides a /Temp Enable drive signal to heater drive 150, which energizes heater 152. In one preferred embodiment, heater 152 is a resistive film heater which is positioned within syringe holder 116 adjacent to syringe body 18.

Computer 100 also receives feedback signals from contrast bottle sensor 160, forward limit sensor 162, reverse limit sensor 164, syringe missing sensor 166, chamber open sensor 168, no contrast bubble detector 170, and air in line bubble detector 172.

Contrast bottle sensor 160 is a miniature switch located within reservoir holder 72. The state of the Contrast Bottle Present signal from sensor 160 indicates whether a reservoir 22 is in position within holder 72. If reservoir 22 is not present, computer 100 will disable the fill operation.

Forward limit and reverse limit sensors 162 sense the end limit positions of plunger 20. When plunger 20 reaches its forward limit position, no further forward movement of plunger 20 is permitted. Similarly, when reverse limit sensor 164 indicates that plunger 20 has reached its reverse limit position, no further reverse movements are permitted.

Syringe missing sensor 166 is a miniature switch or infrared emitter/detector which indicates when syringe body 18 is not in position within syringe holder 16. If syringe body 18 is not in position, all movement functions are disabled except that plunger 20 can move to its reverse limit position (i.e., return to zero).

Chamber open sensor 168 is a miniature switch or infrared emitter/detector which senses when door 70 of syringe holder 16 is open. When the signal from sensor 168 indicates that door 70 is open, all movement functions are disabled. Only when door 70 is closed and locked may any movement be allowed. When door 70 is indicated as closed and sensor 166 indicates the syringe body 18 is in position, other normal functions of the system 10 can proceed.

Bubble detector 170 is positioned between reservoir 22 and top port 78, and is preferably an infrared emitter/detector which senses air bubbles. If an air bubble is sensed in the flow path between reservoir 22 and top port 78 during a fill operation, the fill operation is disabled until a new reservoir is connected.

Bubble detector 172 is positioned to sense air bubbles in high pressure line 28. It is preferably an infrared emitter/detector type of bubble detector. Any air bubble which is sensed in high pressure line 28 results in the disabling of all fluid push out functions, whether the fluid is saline solution from peristaltic pump 44 or contrast material from syringe body 18.

The control system of FIG. 3 also includes the capability to provide a control signal to x-ray equipment through relay 180 which is controlled by computer 100. In addition, computer 100 receives data from blood pressure transducer 38 and from an electrocardiograph (ECG) system which is separate from injector system 10. The Pressure and ECG signals are received through signal conditioners and A/D converter 190, and are transferred to computer 100. The ECG signal is used by computer 100 in one preferred embodiment, to synchronize operation of motor 104 (and thus the Patient Inject operation) with heart beats.

Blood flow to the heart occurs predominantly in diastole (when the heart is between contractions). Continuous injection of contrast material results in spillage of the contrast material into the aorta during systole (during contraction). By injecting primarily during diastole, contrast dosage can be reduced without impairing the completeness of the contrast injection into the coronary artery.

In a preferred embodiment, the injection of radiographic contrast material is synchronized to the coronary artery blood flow. The time periods of systole and diastole are determined using an electrocardiographic (ECG) electrical signal, arterial blood pressure waveform analysis, or other timing based on the heart rate. By controlling speed of motor 104, speed and therefore movement of plunger 20, the injection of contrast material is interrupted during the period of systole, which reduces or stops contrast injection during this time. In combination with remote control 14, the operator can vary the rate of contrast injection into the coronary artery while computer 100 automatically pulses the contrast injection to the cardiac cycle.

The inertial forces of the moving contrast material and expansion of the containers and tubing holding the contrast material and transmitting it to the patient can cause a phase lag between movement of plunger 20 within syringe body 18 and movement of contrast material out of catheter 30 into the patient. To adjust to the phase lag between the plunger 20 movement and contrast expulsion into the patient, a variable time offset can be entered through control panel 54 such that the timing of the cardiac cycle can be offset by a selected time. Since the magnitude of the phase lag may be dependent on the frequency of the heart rate, an algorithm within computer 100 continuously and automatically adjusts the magnitude of the time offset, based on the instantaneous heart rate during the injection of contrast material.

FIG. 4 shows one embodiment of control panel 54 which illustrates the front panel control switches 56 and display 58 of one embodiment of the present invention. Front panel control switches 56 include Set Up/Fill/End switch 200, Purge switch 202, Aspirate switch 204, Saline switch 206, Enable OK switch 208, Injection Volume Limit switches 210a and 210b, Injection Flow Rate Limit switches 212a and 212b, Injection Pressure Limit switches 214a and 214b, Rise Time switches 216a and 216b, OK switch 218, Injection Range Toggle switch 220, Large Injection OK switch 222, and Stop switch 224.

Set Up/Fill/End switch 200 is a momentary, push button switch. When it is first activated, the user will be notified to place syringe 18 in syringe holder 16. When syringe 18 has been placed in syringe holder 16 (which is indicated to computer 100 by sensor 166), the user will be instructed to close and lock the chamber (i.e., to close door 70). Plunger 20 is moved to its full forward position expelling all air within the syringe. Display 58 then indicates to the operator that contrast reservoir 22 should be connected. Once contrast reservoir 22 has been put in place, the operator is requested to depress OK switch 218, at which time plunger 20 will retract at a set rate (preferably corresponding to a flow rate of 10 ml per second) to the maximum syringe volume. If the real speed (as indicated by feedback to computer 100 from A/D converter 116) is greater than the set speed, system 10 will stop.

Once plunger 20 is at its rearward most position, motor 104 is actuated to move plunger 20 forward to purge all air bubbles. Pressure sensor 114 provides an indication of when one-way valve 24 is closed and pressure is beginning to build up within syringe body 18. Once the purge is completed, the total volume injected and the number of injections counter is reset.

The actuation of switch 200 also allows for full retraction and disengagement of plunger 20 from syringe body 18.

Purge switch 202 is a protected momentary push button switch. When activated, Purge switch 202 causes plunger 20 to move forward to expel air through top port 78. The forward movement of plunger 20 is limited and stopped when a predetermined pressure within syringe 18 is reached. This is sensed by pressure sensor 114. The purge operation which is initiated by Purge switch 202 will expel air within syringe 20. The user may also use Purge switch 202 to purge fluid through patient port 84 by depressing and holding Purge switch 202 continuously on.

Aspirate switch 204 is a momentary push button switch which causes computer 100 to activate pump motor 120 of peristaltic pump 44. Pump motor 120 is operated to aspirate catheter 30 at a set speed, with the aspirated fluid being collected in waste bag 52. All other motion functions are disengaged during aspiration. If the real speed of motor 120 is greater than a set speed, computer 100 will stop motor 120.

Saline switch 206 is an alternate action switch. Pump motor 120 is activated in response to Saline switch 206 being pushed on, and saline solution from bag 50 is introduced into manifold 26 and catheter 30 at a set speed. If Saline switch 206 is not pushed a second time to stop the flow of saline solution within 10 seconds, computer 100 automatically stops pump motor 120. If a time-out is reached, Saline switch 206 must be reset to its original state prior to initiating any further actions.

Enable OK switch 208 is a momentary push button switch. After the system has detected a disabling function at the end of an injection other than a limit, Enable OK switch 208 must be activated prior to activating OK switch 218 and initiating any further function.

Injection Volume Limit keys 210a and 210b are pushed to either increase or decrease the maximum injection volume that the system will inject during any one injection. Key 210a causes an increase in the maximum volume value, and key 210b causes a decrease. Once the maximum injection volume limit has been set, if the measured volume reaches the set value, computer 100 will stop motor 104 and will not restart until OK switch 218 has been depressed. If a large injection (i.e., greater than 10 ml) has been selected, OK switch 218 and Large Injection OK switch 220 must both be reset prior to initiating the large injection.

Injection Flow Rate Limit keys 212a and 212b allow the physician to select the maximum flow rate that the system can reach during any one injection. If the measured rate (which is determined by the feedback signals from tachometer 108 and potentiometer 111) reaches the set value, computer 100 will control motor 104 to limit the flow rate to the set value.

Injection Pressure Limit keys 214a and 214b allow the physician to select the maximum pressure that the system can reach during any one injection. If the measured pressure, as determined by pressure sensor 114, reaches the set value, computer 100 will control motor 104 to limit the pressure to the injection pressure limit. The injection rate will also be limited as a result.

Rise Time keys 216a and 216b allow the physician to select the rise time that the system will allow while changing flow rate during any one injection. Computer 100 controls motor 104 to limit the rise time to the set value.

In alternative embodiments, keys 210a–210b, 212a–212b, 214a–214b, and 216a–216b can be replaced by other devices for selecting numerical values. These include selector dials, numerical keypads, and touch screens.

OK switch 218 is a momentary push button switch which resets functions and hardware sensors. In response to OK switch 218 being activated, computer 100 controls display 58 to ask the operator to acknowledge that the correct function has been selected. Activation of OK switch 218 causes the status to be set to Ready.

Injection Range switch 220 is a toggle switch. Depending on whether switch 220 is in the "small" or "large" position, it selects either a high or a low injection volume range for the next injection.

Large Injection OK switch 222 is a momentary push button switch. When the large injection range has been selected by injection range switch 220, the Large Injection OK button 222 must be activated to enable OK switch 218. OK switch 218 must be activated prior to each injection. On large volume injections, the user is required to verify the volume selected by activating first Large Injection OK switch 222 and then OK switch 218.

Stop switch 224 is a momentary push button switch. When stop switch 224 is pushed, it disables all functions. Display 58 remains active.

Display panel 58 includes Set-Up display 250, Status display 252, Alerts display 254, Limits display 256, total number of injections display 260, total volume injection display 262, flow rate display 264, injection volume display 266, injection volume limit display 268, injection rate limit display 270, pressure limit display 272, rise time minimum display 274, large injection display 276, and real time clock display 278.

Set-Up display 250 contains a series of messages which are displayed as the operator goes through the set up procedure. The display of messages in set up display 250 are initiated by the actuation of set up switch 200 as described previously.

Status display 252 provides a flashing indication of one of several different operating conditions. In the embodiment shown in FIG. 4, these status conditions which can be displayed include "Ready", "Set-Up", "Injecting", "Filling" "Flushing", and "Aspirating".

Alerts display 254 and Limits display 256 notify the operator of conditions in which system 10 has encountered a critical control parameter and will disable operation, or has reached an upper or lower limit and will continue to function in a limited fashion, or has reached an upper or lower limit and will continue to operate.

Total number of injections display 260 displays the total number of injections (cumulative) given for the current patient case. The cumulative total volume injected during the current patient case is displayed by total volume display 262.

Displays 264 and 266 provide information on the current or last injection. Display 264 shows digital value of the real time flow rate to the patient during injection. Once the injection is completed, the value displayed on display 264 represents the peak flow rate reached during that injection. Display 266 shows the digital value of the volume injected during the most recent injection.

Display 268 displays the digital value of the maximum injection volume selected by operation of switches 210a and 210b. Similarly, display 270 shows the digital value of the maximum flow rate that the system will allow, as selected by switches 212a and 212b.

Display 272 shows the digital value of the maximum pressure that the system will allow to be developed in syringe 18. The pressure limit is selected by switches 214a and 214b.

Display 274 displays the minimum rise time that the system will allow while changing flow rate. The minimum rise time is selected through switches 216a and 216b.

Large injection display 276 provides a clear indication when the large injection scale has been selected by the operator.

Real-time clock display 278 shows the current time in hours, minutes, and seconds.

Figure 5A:
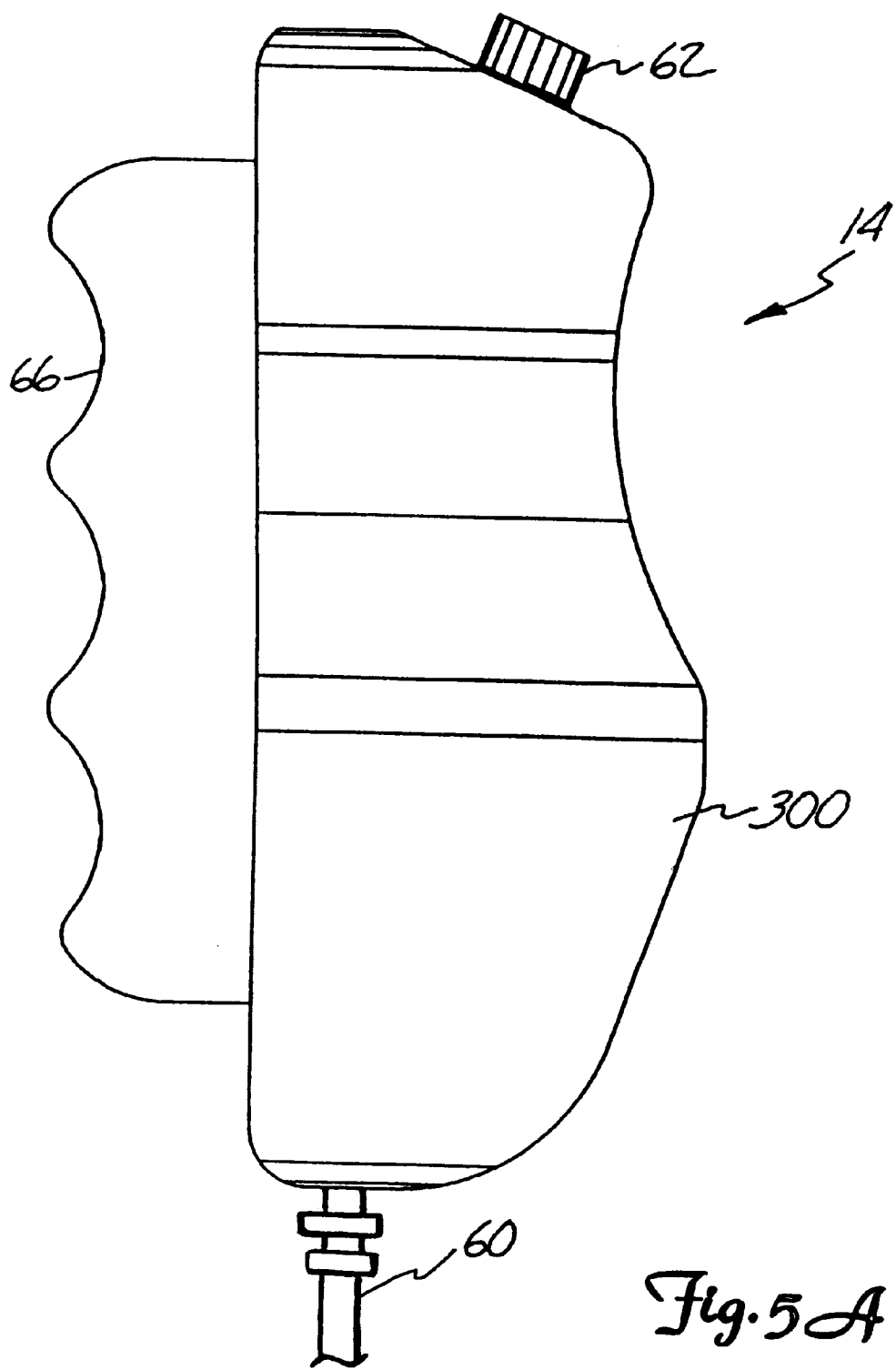
FIGS. 5A and 5B are side and partial top perspective views of the remote control of the system of FIG. 1.
Figure 5B:
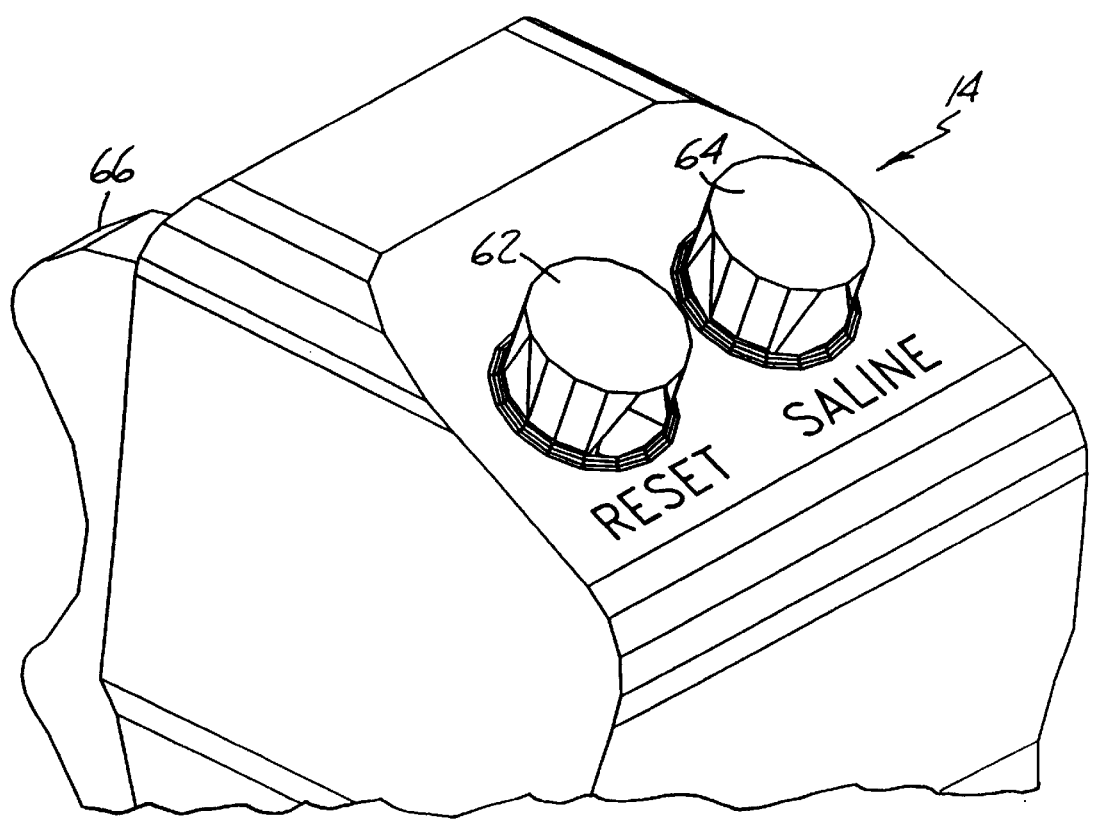
Figure 6:
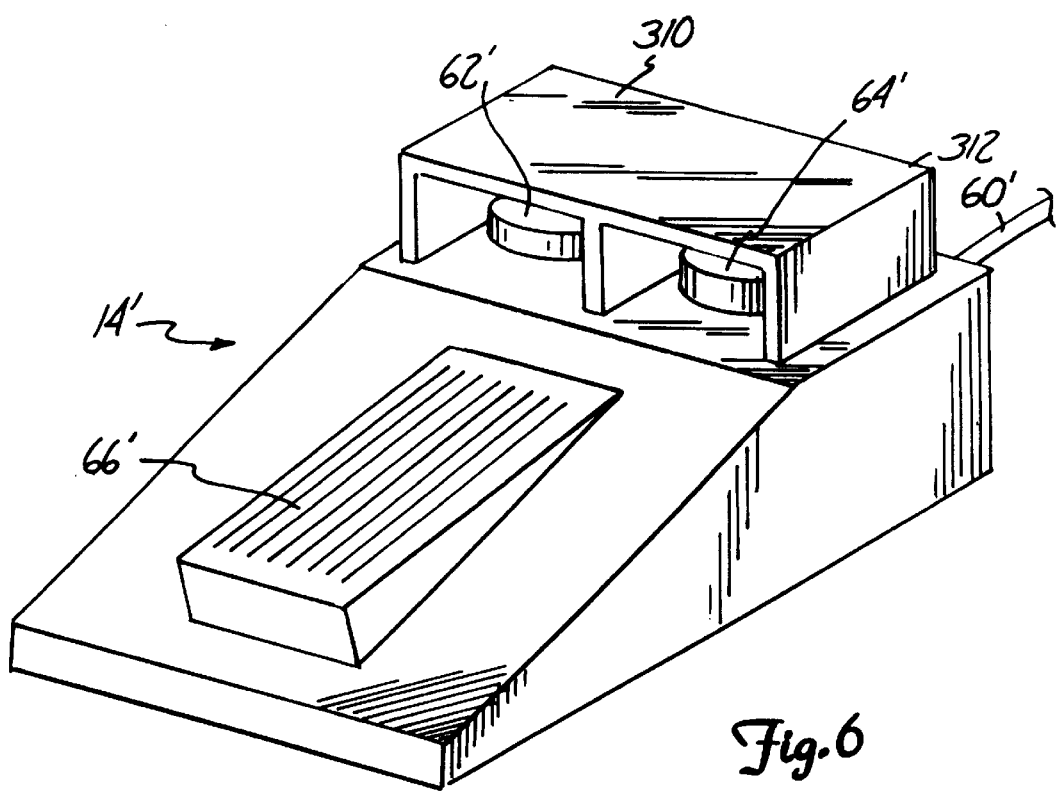
FIG. 6 is a perspective view of a foot operated remote control.

FIGS. 5A and 5B show remote control 14 which includes main housing 300, which is designed to conform to the user's hand. Trigger 66 is movable with respect to housing 300, and the position of trigger 66 generates a command signal which is a function of trigger position. In one embodiment, trigger 66 is linked to a potentiometer within housing 300. The command signal controls the injunction flow rate or speed. The flow rate is directly proportional to trigger position.

Reset switch 62 is a momentary push button switch whose function is identical to that of OK switch 218. Alternatively, Reset switch 62 may also be labeled "OK".

Saline switch 64 on remote control 14 is an alternate action push button switch which is pushed to turn on and pushed again to turn off. The function of Saline switch 62 is the same as that of Saline switch 206 on front panel 54.

As illustrated in another embodiment of the present invention, an alternative remote control 14' in the form of a foot pedal is used instead of the hand held remote control 14 illustrated in FIG. 1 and in FIGS. 5A and 5B. Foot pedal remote control 14' includes foot operated speed pedal or trigger 66' for providing a command signal, as well as Reset or OK switch 62' and Saline switch 64'. Covers 310 and 312 protect switches 62' and 64' so that they can only be actuated by hand and not accidentally by foot. Foot pedal remote control 14' is connected to console 12 by cable 60', but could alternatively be connected by a wireless link.

FIGS. 7A–7D and FIGS. 8A–8C illustrate the construction and operation of one way valve 24 and manifold 26 during Contrast Fill, Air Purge and Patient Injection operation.

FIGS. 7A and 8A illustrate one way or check valve 24, manifold 26, syringe body 18, and plunger 20 during a Contrast Fill operation. Inlet check valve of one way valve 24 includes weighted ball 350 which is positioned at its lower seated position within valve chamber 352 in FIGS. 7A and 7B. Contrast material is being drawn into syringe body 18 by the rearward movement of plunger 20. The contrast material flows through passages 354 around ball 350 and into upper port 78.

Manifold 26 contains spring loaded spool valve 360, which includes spool body 362, shaft 364, O-rings 366, 368 and 370, bias spring 372, and retainer 374. As shown in FIG. 7A, during the Contrast Fill operation, bias spring 372 urges spool body 362 to its right-most position toward syringe body 18. In this position, spool body 362 blocks lower port 80 of syringe body 18 while connecting transducer saline port 82 to patient port 84 through diagonal passage 376. O-rings 366 and 368 on the one hand, and O-ring 370 on the other hand, are positioned on the opposite sides of diagonal passage 376 to provide a fluid seal.

FIGS. 7B and 8B illustrate the Air Purge operation. Syringe body 18 has been filled with contrast fluid, but also contains trapped air. Plunger 20 is driven forward to force the air out of syringe body 18 through upper port 78 and through check valve 24. The force of the air may cause a slight lifting of ball 350 in check valve 20. Ball 350, however, is sufficiently heavy that the air being forced out of syringe body 18 and back toward reservoir 22 cannot lift ball 350 into its uppermost seated position where it would block the flow of air out of syringe body 18.

During the Air Purge operation, spool valve 360 is in the same position as in FIG. 7A. Diagonal passage 376 connects transducer saline port 82 with patient port 84. As a result, pressure monitoring by pressure transducer 38 can be performed during the Air Purge (as well as the Contrast Fill) operation.

FIGS. 7C and 8C illustrate the state of manifold 26 and check valve 24 at the end of the Air Purge operation and at the beginning of a Patient Inject operation.

In FIG. 7C, all air has been expelled from syringe body 18. Ball 350 floats on the radiographic contrast material, so that when all air has been removed and the radiographic contrast material begins to flow out of syringe body 18 and through upper port 78 to valve chamber 352, ball 350 is moved upwards to its upper seated position. Ball 350 blocks any continued upward flow of radiographic contrast material, as is illustrated in FIGS. 7C and 8C.

In the state which is illustrated in FIG. 7C, the pressure within syringe body 18, and specifically the pressure in lower port 80 has not yet reached a level at which the bias force of spring 372 has been overcome. As a result, spool body 362 has not yet moved to the left and diagonal passage 376 continues to connect transducer saline port 82 with patient port 84.

FIG. 7D illustrates the patient inject operation. Plunger 20 is moving forward, and inlet check valve 24 is closed. The pressure at lower port 80 has become sufficiently high to overcome the bias force of spring 372. Spool body 362 has been driven to the left so that lower port 80 is connected to patient port 84. At the same time spool body 362 blocks transducer/saline port 82.

By virtue of the operation of spool valve 360, the high pressure generated by movement of plunger 20 and syringe body 18 is directly connected to patient port 84, while saline port 82 and pressure transducer 38 are protected from the high pressure. The pressure to actuate may be variable and determined after manufacture by increasing or decreasing the syringe preload.

FIGS. 9–11B illustrate another embodiment of the dual port syringe in the present invention. In this embodiment, conventional syringe body 400 is modified to provide dual port functionality. The modification is accomplished by adapter insert 402 and T-connector 404.

Figure 10:
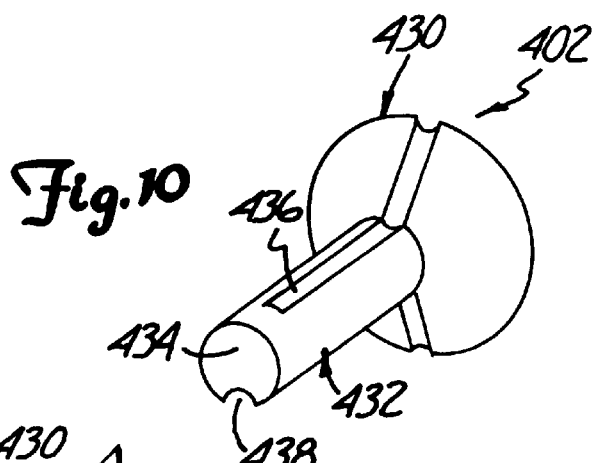
FIG. 10 is a perspective view of an adapter insert used in the dual port syringe of FIG. 9.
Figure 11A:
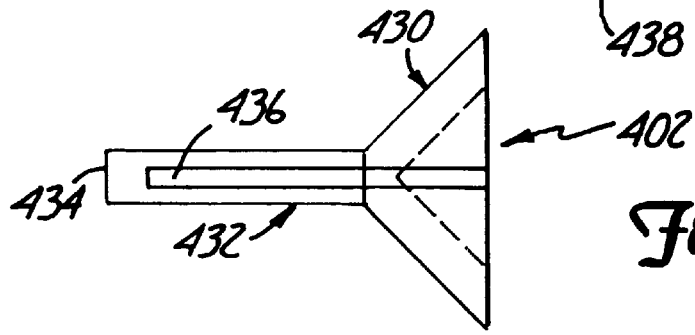
FIGS. 11A–11B are top and side views of the adapter insert of FIG. 10.
Figure 11B:
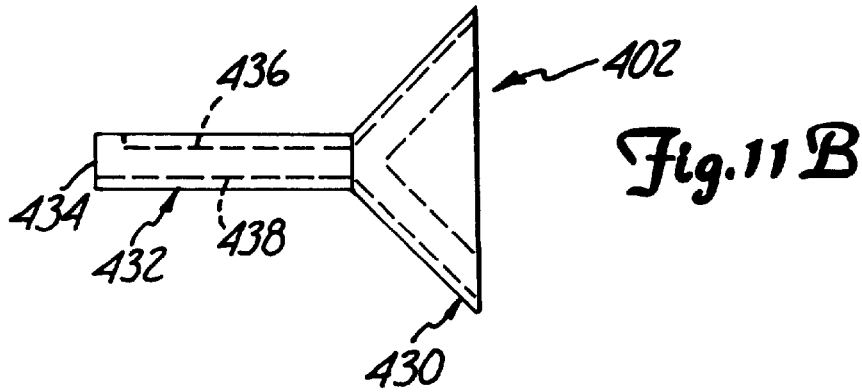

Syringe body 400 has a cylindrical side wall 410, frustoconical end wall 412, and tubular end port 414. Adapter insert 402, which is shown in more detail in FIGS. 10 and 11 is inserted into syringe body 400 so that it mates with end wall 412 and tube 414. T-connector 404 connects to the end of tube 414, and provides upper port 420 and lower port 422.

Adapter insert 402 has a frustoconical flange 430 and a generally cylindrical shaft 432. Flange 430 mates against the inner surface of end wall 412 of syringe body 400. Shaft 432 extends through tube 414 and through T-connector 404, so that end surface 434 of shaft 432 is generally located at the distal end of T-connector 404. Upper port groove 436 extends along the upper surface of shaft 432 and the inclined upper surface of flange 430. Upper port groove 436 stops just short of end 434.

Lower port groove 438 extends the entire length of shaft 432, along its lower surface, and then extends downward on the inclined lower surface flange 430.

Figure 9:
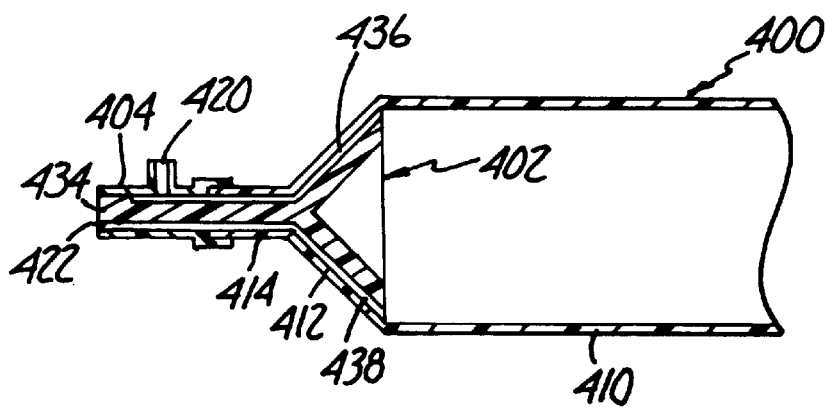
FIG. 9 shows a conventional syringe body adapted for dual port

When adapter insert 402 is positioned within syringe body 400 as shown in FIG. 9, it forms a close press fit with both syringe body 400 and T-connector 404. Upper port groove 436 provides an upper port passage which extends from port 420 to the interior of syringe body 400. As shown in FIG. 9, upper port groove 436 opens into the interior of syringe body 400 at the uppermost portion of the interior.

Lower port groove 438 extends from the distal end of T-connector 404 to the lowermost position in the interior of syringe body 400.

The embodiment of the present invention shown in FIGS. 9–11B provides an inexpensive adaptation of a conventional syringe body so that it can exhibit the advantages of dual port capability.

In conclusion, the angiographic injector system of the present invention provides interactive control of the delivery of radiographic contrast material to a catheter through a user-actuated proportional control. This allows the user to adjust the flow rate of contrast material interactively as needed and as the patient's condition changes.

Although the present invention has been described with reference to preferred embodiments, workers skilled in the art will recognize that changes may be made in form and detail without departing from the spirit and scope of the invention. For example, syringe holder 16 may take other forms, such as an end loaded cylinder. Similarly, manifold 26 can take other configurations and can incorporate, for example, a part of ports 78 and 80.

B. Detailed Description of the Present Invention

FIGS. 12–17 depict one preferred syringe 500 usable in the angiographic system described above. Syringe 500 includes a syringe body 502 having a wall defining first and second opposite ends 504, 506. The first end 504 corresponds to a distal end of syringe 500, and the second end 506 corresponds to a proximal end of syringe 500. The wall of body 502 is cylindrical in the illustrated embodiment and includes a central axis 508 extending longitudinally therethrough.

Syringe body 502 defines a pumping chamber 510 in an interior thereof. A wiper or plunger 512 is located in the pumping chamber 510 and is constructed and arranged for reciprocal motion between a position adjacent to first end 504 and second end 506. That is, when syringe 500 is mounted in a system analogous to the angiographic system described herein above, an actuator from the system energizes the plunger and causes it to move between the second end 506 and the first end 504. The plunger 512 is supported by a plunger support member 617. Member 617 preferably comprises a rigid, hard material, for example, an ABS plastic, to interface between an actuator and the plunger 512. Member 617 attaches to plunger 512 by, preferably, a snap fit.

Syringe 500 includes an end wall 514 located at the first end 504 of the syringe body 502. End wall 514 is located generally normal to the central, longitudinal axis 508 of syringe 500. The end wall 514 includes a flat face 516. The flat face 516 is particularly adapted for mating engagement with a syringe holder, to be described further below, in an angiographic system as described above. Flat face 516 is advantageous in the preferred arrangement. In the angiographic system as described herein, significant thrust loads must be borne in order to suitably inject the contrast material into the cardiovascular system of the patient. Flat face 516 allows the thrust load from the injections to be distributed in a manageable fashion. An angled face, in contrast, would create a wedge action, which would unnecessarily stress the syringe and create an unnecessary side load in the syringe holder. The inventors have recognized that a spherical or cone face would require a large door in the syringe holder to support the thrust and would also require some elaborate mechanism to properly position the door against the syringe. Flat face 516 on syringe 500, however, allows the thrust load to be managed by a thin flat door, to be described in more detail below, and is able to bear the thrust load from the angiographic injections.

Syringe 500 defines at least one port for providing fluid flow communication with pumping chamber 510. In the particular embodiment illustrated, syringe 500 includes two ports providing fluid flow communication with the pumping chamber 510. Specifically, an inlet port 518, FIG. 14, allows the pumping chamber 510 in syringe 500 to be filled with contrast material, and purged or air through inlet port 518, allowing for an infinite capacity syringe. By "infinite capacity" it is meant that syringe 500 continues to take in contrast media from a bottle of contrast media; the bottles being replaced when empty. A housing 520 circumscribes inlet port 518 and allows inlet port 518 to be connected with an appropriate bottle 602 of contrast fluid. When syringe 500 is oriented in a syringe holder in an angiographic system as described above, syringe 500 defines a top portion and a bottom portion. FIG. 15 illustrates the orientation of syringe 500 as it would be mounted in an angiographic system of the preferred embodiment. When in such an orientation, the inlet port 518 is located in the top portion 522 of syringe 500.

In preferred embodiments, the syringe 500 is mounted in an angiographic system such that the syringe 500 angles somewhat from the horizontal. By angling the syringe 500 from the horizontal, air is allowed to gather around the inlet port 518 in order to be expelled through the inlet port 518 during an air purge operation. Angles within the range of about 5–30°, and preferably about 10–15° from the horizontal are preferable.

Inlet housing 520 houses a valve assembly analogous to check valve 24, described and illustrated above. Check valve 24 is competent to fluid, and incompetent to air. That is, check valve 24 permits air to be expelled or purged from the syringe 500, but does not allow fluid to flow out of the pumping chamber 510 and back into the bottle 602 of contrast fluid when pressure movement is applied on the syringe side of the check valve 24.

Syringe 500 also includes an outlet port 524, FIG. 16, in fluid flow communication with pumping chamber 510. Outlet port 524 permits fluid flow from pumping chamber 510 to downstream fluid passageways, and ultimately into the patient's cardiovascular system. Outlet port 524 is surrounded, or circumscribed, by outlet port housing 526 extending, or projecting, from end wall 514. The outlet port housing 526 is adapted, i.e., constructed and arranged, to receive an outlet tube. Outlet port 524 and outlet housing 526 are analogous to lower port 80, described in detail above.

When syringe 500 is oriented in the preferred angiographic system of the present invention, the outlet port 524 is located adjacent to the bottom portion 523 of syringe 500.

The syringe end wall 514 includes an interior portion 528, FIG. 17, and an exterior portion 530, FIG. 14. It is the exterior portion 530 which defines the flat face 516 of syringe 500. The exterior portion 530 includes a plurality of ribs 532. In the embodiment illustrated, there are seven ribs 532 extending transversely across the end wall 514. Ribs 532 help to provide a reinforcing function. Ribs 532 also provide an attractive, ornamental appearance to syringe 500.

Ribs 532 each have end portions 534 terminating in a plane transverse to longitudinal axis 508 of syringe body 502. The end portions 534 define the flat face 516.

The interior portion 528 defines a cone-shaped surface 536, FIG. 17. This cone-shaped surface 536 is illustrated in FIG. 17 by the shading therein. Cone-shaped surface 536 helps to direct the liquid in pumping chamber 510 to an appropriate fluid port.

Preferred dimensions for syringe 500 are described herein below. Syringe body 502 has a diameter of about 1.3 inches. The length of syringe body 502 between first end 504 and second end 506 is about 6–7 inches. The inside of syringe body 502 is tapered so that second end 506 has an inside diameter greater than the inside diameter of interior portion 528 of the end wall 514. This taper is about 0.1° from horizontal for the majority of its length. The angle of tapering increases to about 1° at a point about 1 inch from the second end 506 of syringe 500. The interior portion 528 defining the cone-shaped surface 536 slopes at an angle of about 27° from vertical, and the vertex of the cone is rounded at a radius of about 0.25 inches. Each of ribs 532 is about 0.1 inches thick. The ribs 532 are spaced about 0.12 inches apart. The outlet port housing 526 has an outer diameter of about 0.3 inches, and an inner diameter of about 0.2 inches. The longitudinal axis of the outlet port housing 526 is parallel to and about 0.5 inches lower than the central longitudinal axis 508 of syringe body 502. The outlet port housing 526 is arranged relative to the syringe body 502, such that the outer diameter of the outlet port housing 526 intersects at a tangent point of the diameter of syringe body 502. The inlet port housing 520 has an outer diameter of about 0.4 inches and an inside diameter of about 0.2 inches. The longitudinal axis of the inlet port housing 520 is tilted about 10° from vertical toward the end wall 514. The inlet port 518 has a diameter of about 0.1 inches. The inlet port housing 520 is about 0.5 inches long measured from where the inlet housing 520 meets the syringe body 502 in the top portion 522 of the syringe 500.

Figure 18:
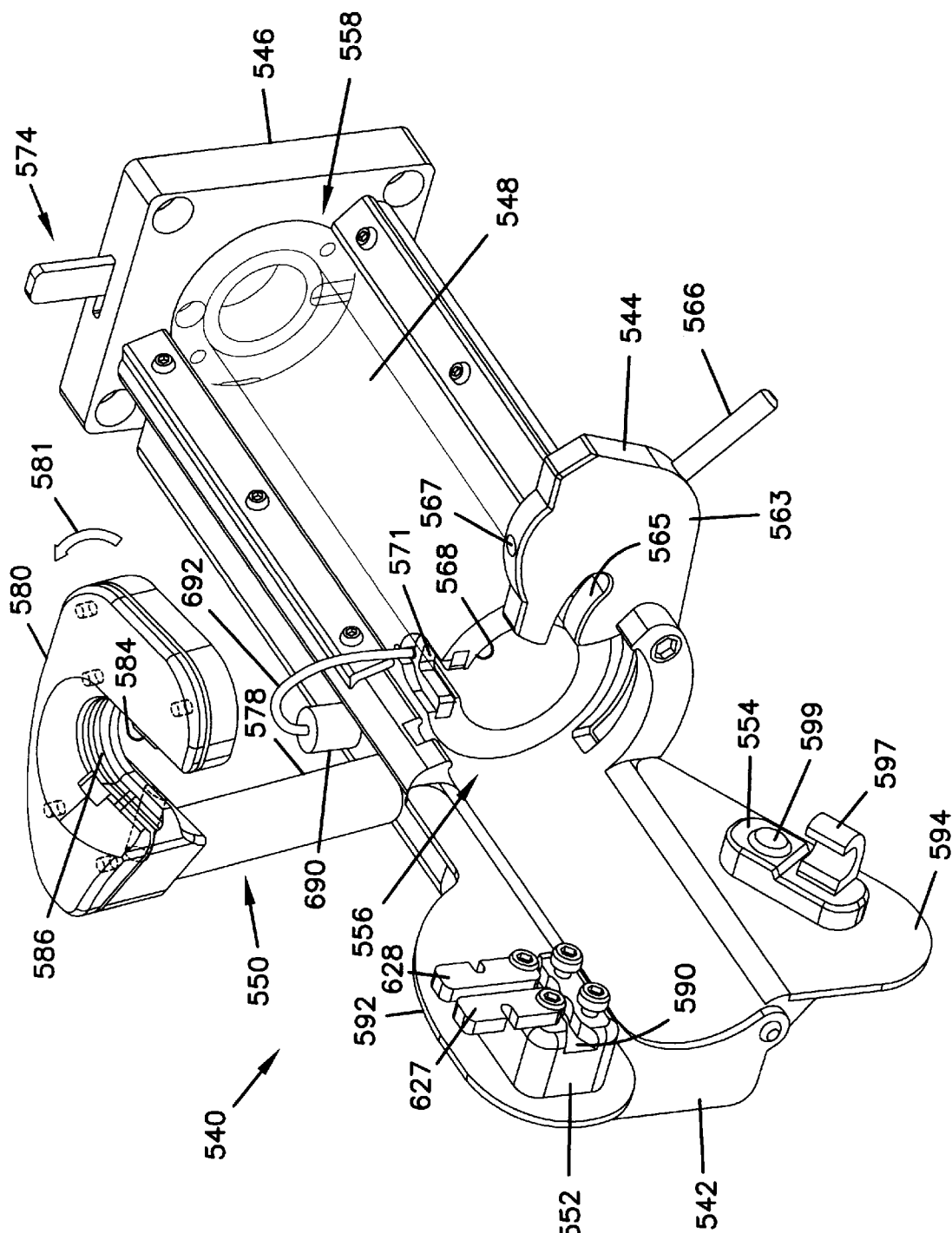
FIG. 18 is a perspective view of one embodiment of a syringe holder arrangement, according to the present invention.
Figure 19:
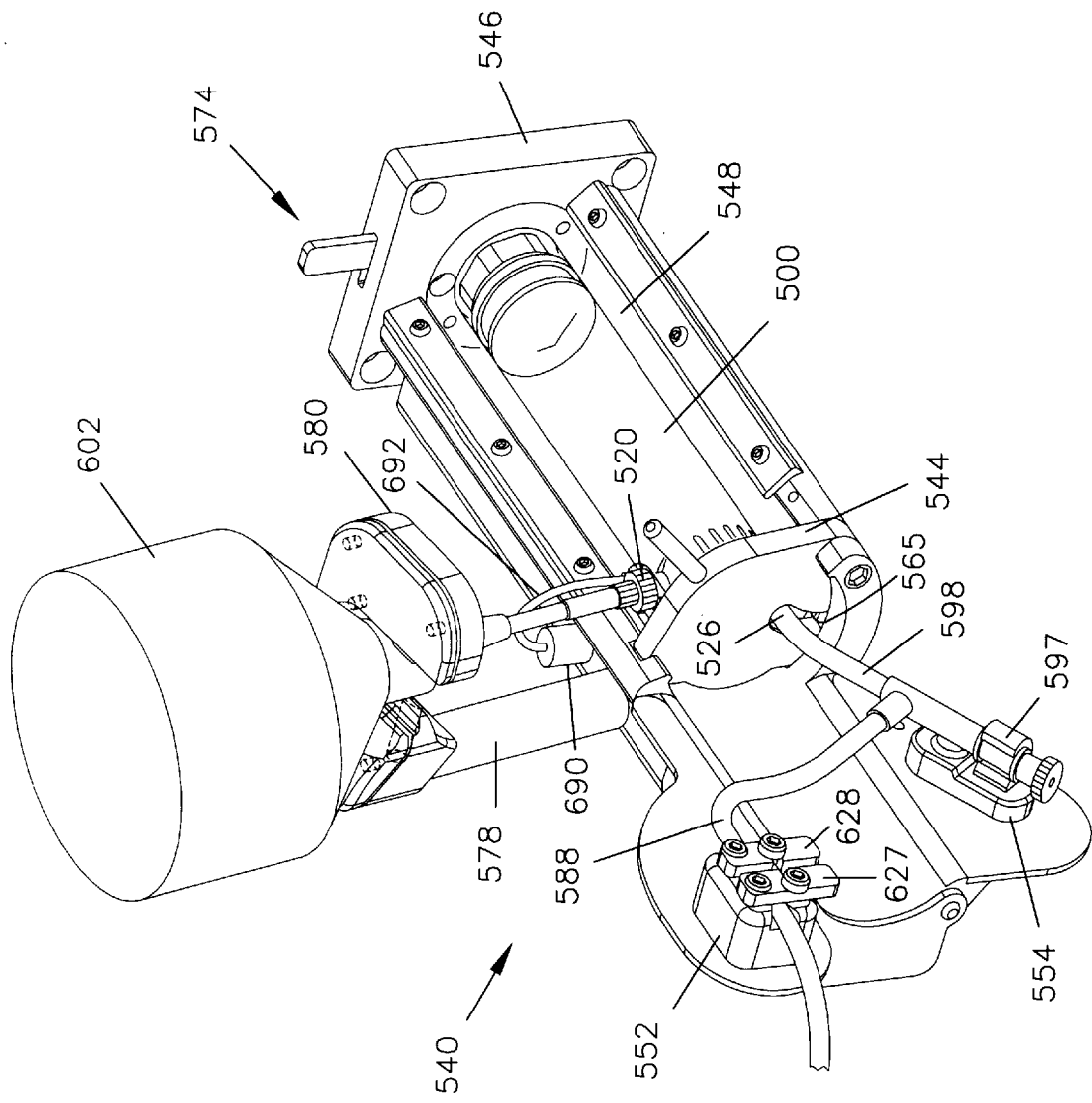
FIG. 19 is a perspective view of the syringe holder arrangement depicted in FIG. 18, and holding a syringe and a bottle of fluid.
Figure 20:
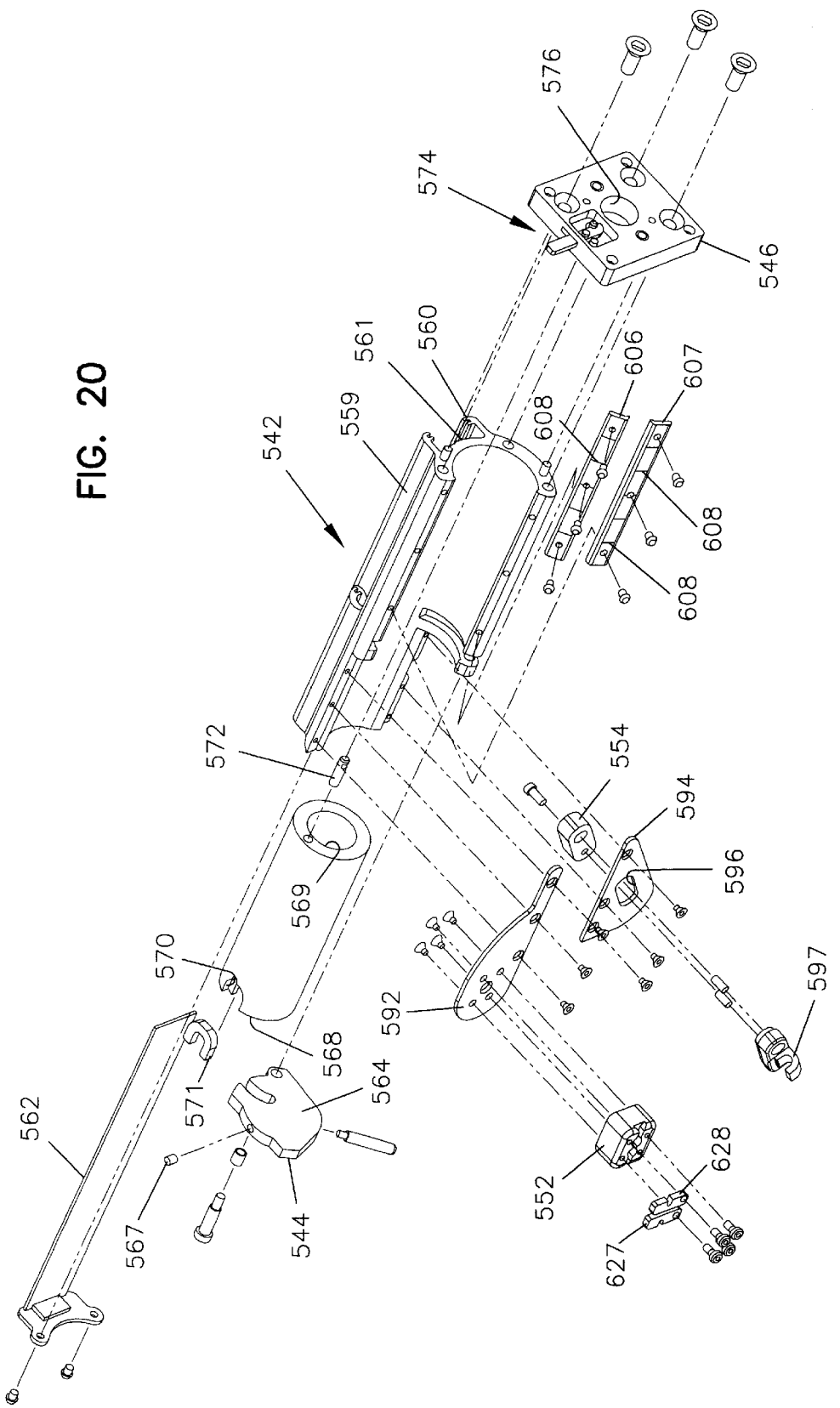
FIG. 20 is an exploded, perspective view of a subassembly of the syringe holder arrangement depicted in FIG. 18.

In reference now to FIGS. 18–20, a syringe holder arrangement is illustrated generally at 540.

In general, the syringe holder arrangement 540 includes a mounting chamber body 542; a door member 544; a rear plate 546; and a pressure containment sleeve 548. Preferred assemblies further include a bottle holder assembly 550; an air column detector 552; and a manifold holder 554.

Mounting chamber body 542 is for holding the syringe in place during an angiographic operation. The mounting chamber body 542 is constructed and arranged to be durable enough to sustain large pressure loads from the fluid push through syringe 500. Mounting chamber body 542 has an arcuate configuration for receipt of sleeve 548. It includes a loading end 556 for receipt of syringe 500, and an actuating end 558 for receiving the actuator to reciprocate the syringe plunger 512 between its respective proximal and distal positions within syringe 500. The loading end 556 also corresponds to the front of the mounting chamber body 542, and the actuating end 558 corresponds to the back or rear of the mounting chamber body 542.

Preferably, the mounting chamber body 542 comprises a series of layers in order to provide a convenient and preferred structure for holding syringe 500. In particular, the outermost layer is an electroilluminescent layer. The electroilluminescent layer permits illumination of the mounting chamber body 542 and the associated tubing. That is, the electroluminescent layer illuminates the fluid pathway of the contrast material as it is being conveyed from the syringe 500 to downstream components and ultimately into the patient's cardiovascular system.

Adjacent to the electroilluminescent layer is a membrane heating element. This layer maintains heat of the contrast fluid in order to sustain a desired viscosity in the contrast fluid for conveying into the patient's cardiovascular system.

The next layer of the mounting chamber body 542 and adjacent to the membrane heating element layer is a layer of foam. The foam layer keeps contact resistance with the syringe 500 high and thermal resistance low. It functions to take up tolerances and helps to snugly hold the syringe 500 in place in the syringe holder arrangement 540.

The last layer of the mounting chamber body 542 is an aluminum extrusion. It provides for a rigid shape and for convenient manufacturing. A layer of adhesive attaches the foam layer to the aluminum extrusion.

As illustrated in FIG. 20, the mounting chamber body 542 includes a pair of back flanges 559, 560 defining a groove 561 therebetween. The groove 561 provides for storage and containment of wires to the syringe holder arrangement 540. A plate 562 slides in groove 561 and is securably attached thereto to provide for neat and convenient storage.

Still referring to FIG. 18, door member 544 is provided to allow for selective opening and closing of the loading end 556 of body 542. That is, door member 544 is movable relative to mounting chamber body 542 between positions allowing access to mounting chamber body 542, and into the interior of sleeve 548, and a position which blocks, or closes access to, the interior of sleeve 548. In the position where it closes access, door 544 provides for a stop surface to support and resist the load applied through the syringe 500 when the plunger is depressed.

In the particular embodiment illustrated, the door member 544 is pivotable relative to the mounting chamber body 542. This allows for quick and convenient loading and unloading of syringe 500 into the holding arrangement 540. When the door 544 is in its closed position, FIG. 19, it locks the syringe 500 into place in the holder arrangement 540.

In reference again to FIG. 18 and FIG. 20, door member 544 is a structure with a pair of flat, planar, opposite surfaces 563, 564. Preferably, it is an a fabricated stainless steel plate with a thickness of about 0.4–1 inches. Flat surface 564, FIG. 20, is constructed and arranged for a sliding, abutting engagement with the flat end wall 514 of syringe 500 and pressure sleeve 548. It also slides relative to and abuts against the end surface of sleeve 548. Because of the geometry of the flat face 516 of the end wall 514 of syringe 500, the thrust load exerted by the angiographic system 10 through syringe 500 can be managed by the flat door member 544.

In reference again to FIG. 18, door member 544 defines a channel, groove, or slot 565. Slot 565 is an open, through-hole penetrating door member 544 and extending to the edge of door member 544. Slot 565 provides for slidable communication with outlet port housing 526 of syringe 500. That is, when syringe 500 is oriented properly for loading in holding arrangement 540, after syringe 500 is resting within sleeve 548, as door member 544 is pivoted to the closed position, FIG. 19, outlet port housing 526 slides within groove 565. Groove 565 permits the outlet port housing 526 to extend and penetrate through door member 544 to permit liquid from syringe 500 to be conveyed to downstream components.

Still referring to FIG. 18, door member 544 includes a handle 566. Handle 566 extends from a side edge of door member 544 and allows for a user to conveniently pivot the door member 544 between its closed position and its open positions. Door member 544 pivots about its lowest point preventing door member 544 from acting as a guillotine when acted upon by gravity. That is, the arrangement of the door member 544 relative to its pivot point prevents injury to fingers.

In accordance with the invention, a door open sensor is provided. The door open sensor tells the user or operator if the door member 544 is in an open position. That is, it functions as a safety feature such that the angiographic system 10 will not be operated if door member 544 is not in a securely closed position. In the particular embodiment illustrated, the door open sensor includes a magnet 567 in the door member 544, and a Hall effect sensor in the mounting chamber body 542. When door member 544 is pivoted to its closed position, FIG. 19, magnet 567 is in contact with mounting chamber body 542. The Hall effect sensor senses the presence of magnet 567 and provides an indication to the operator that the door member 544 is closed. When the Hall effect sensor does not sense the presence of magnet 567, it provides a signal to the operator that the door member 544 is not in the closed position, but in an open position. One suitable sensor is Hall effect sensor 55449A, available from Microswitch (a division of Honeywell).

Still referring to FIG. 18, the pressure containment sleeve 548 is provided in the holding arrangement 540 to hold syringe 500 snugly between door member 544 and rear plate 546. Sleeve 548 helps to contain the pressure exerted through the syringe 500, and allows for large pressure forces through the syringe 500. The close fit between rear plate 546 and door member 544 holds the syringe 500 so that no forward/rearward movement is allowed.

In the particular embodiment illustrated, sleeve 548 is constructed and arranged to fit, or slide in the mounting chamber body 542. In the preferred embodiment, sleeve 548 is cylindrical, or tubular in shape with first and second open ends 568, 569 (FIG. 20). Sleeve 548 is preferably constructed from a strong, durable, basically transparent material in order to sustain large pressure loads and allow for visibility of the syringe therethrough. One preferred material includes polycarbonate.

In reference to FIG. 19, the first end 568 of sleeve 548 is open and allows the outlet port housing 526 to project, or extend therefrom and through slot 565 in door member 544. Second end 569, FIG. 20, permits an actuator from angiographic system 10 to penetrate sleeve 548 and access the syringe plunger support member 617.

Referring again to FIGS. 18 and 19, it can be seen that door member 544 slides relative to the first end 568 of the sleeve 548, as door member 544 is moved between its closed position and open positions.

Sleeve 548 defines an open groove, or channel 570 extending from the first end 568. Channel 570 accommodates a sensor 571. Sensor 571 is oriented relative to the valve assembly in the inlet housing 520 in order to detect the state of the check valve. That is, sensor 571 detects whether the ball in the check valve is seated in its lowermost position or whether it has been moved out of its lowermost position. In the particular arrangement illustrated, the sensor 571 is an emitter/detector interruptable infrared photodetector device. When the ball interrupts the infrared beam, a signal is sent indicating that the ball is seated in its lowermost position or seat. When the ball is moved out of its lowermost position or seat, the infrared beam is not interrupted, and a signal is generated which indicates that the ball is out of its lower seat.

A connector 690 and wire 692 energize the sensor 571. That is, connector 690 connects the electrical components and wires within groove 691 to the sensor 571.

As can be seen in FIGS. 18 and 20, sensor 571 is generally U-shaped. The U-shape, in addition to enabling detecting of the ball in the check valve, also allows the inlet port housing 520 to be accommodated within sleeve 548 in holding arrangement 540. As illustrated in FIG. 19, when syringe 500 is loaded into holding arrangement 540, it is slid through sleeve 548, and sensor 571 permits inlet port housing 520 to rest within the U-shape of the sensor 571 and extend radially from sleeve 548. In this way, fluid communication is permitted from the source of contrast fluid and into syringe 500, even after syringe 500 is loaded within the holding arrangement 540. One type of sensor 571 useable is an infrared diode (part number SE-1450-004L) and photo-transistor pair (part number SD-1440-004L), both available from Microswitch (a division of Honeywell).

In the preferred embodiment, the sleeve 548 is conveniently removable from the mounting chamber body 542. In this manner, it may be cleaned and disinfected separate from the chamber body 542. In the particular embodiment illustrated in FIG. 20, sleeve 548 is slidable relative to mounting chamber body 542 and can be lockably secured thereto through the cooperation of a locking pin 572 and a locking assembly 574 in the rear plate 546. Locking pin 572 extends from second end 569 of sleeve 548. Locking assembly 574 is a spring loaded locking member that engages and holds pin 572.

Again, in reference to FIG. 18, the rear plate 546 is secured to the mounting chamber body 542 and is in covering relation to the second end 569 of the sleeve 548. Rear plate 546 supports the actuating end 558 of the mounting chamber body 542.

In the particular embodiment illustrated, rear plate 546 has a rectangular configuration. Preferably, it is an aluminum fabricated plate, with a thickness of about 0.6 inches.

In reference now to FIG. 20, rear plate 546 defines an aperture 576 in a central portion therethrough. Aperture 576 allows access to the interior of sleeve 548. That is, aperture 576 permits the angiographic actuator to penetrate and move the syringe plunger 512 between its respective proximal ends and distal ends of syringe 500.

In reference now to FIGS. 18 and 19, the bottle holder assembly 550 is provided to hold a bottle 602 of contrast fluid in order to quickly and conveniently provide a constant source of contrast media to the syringe 500 when it is loaded in holding assembly 540.

In the illustrated embodiment, bottle holder assembly 550 is secured to mounting chamber body 542. Bottle holder assembly 550 includes a column 578 and a neck portion 580.

Neck portion 580 is pivotable with respect to mounting chamber body 542 in the direction of arrow 581. The pivotable nature of neck portion 580 aids the ease of connecting the tubing from the bottle 602 of contrast media to the inlet housing 520 of the syringe 500.

Neck 580 includes universal detail 584 within grooves 586. Universal detail 584 is preferably a spring loaded configured member which allows bottle holder 550 to accommodate and hold bottles of various sizes.

In accordance with the invention, an indicator arrangement is provided to provide information whether a bottle is in the bottle holder assembly 550. In the preferred embodiment, a switch is provided in the universal detail 584.

When a bottle 602 of contrast is within the neck 580, the bottle 602 presses against the spring in the universal detail 584, which actuates the switch. When the switch is actuated, it provides a visual signal to the system operator that a bottle is in fact in the bottle holder assembly 550. If the switch is not actuated, a signal is provided to the user that there is no bottle in the holder assembly 550. One suitable switch is a microswitch MMGGDILOO, available from C&K.

In accordance with the invention, a sensor is provided to indicate if the fluid level in the bottle 602 of contrast is either below a certain level or empty. Preferably, the sensor includes a sensor provided within groove 586 in neck 580. The sensor detects when the fluid level in the bottle 602 has dropped below the level of the sensor in the neck 580. Preferably, the sensor is a reflective, infrared device. One type of sensor useable is infrared sensor H0A1405-2, available from Microswitch (a division of Honeywell).

In reference again to FIGS. 18 and 19, air column detector 552 is provided to detect the presence of air in the fluid line 588 (FIG. 19). Air column detector 552 is analogous to air bubble detector 172, described above. It uses ultrasonic means to detect the presence of air in the line 588. One suitable ultrasonic means is available from Introtek of New York.

Air column detector 552 defines a groove 590, FIG. 18, which provides a friction fit with fluid line 588. That is, the tubing snaps into groove 590 where it is securely held therein. Holders 627, 628 swing down over fluid line 588 to secure it in place (FIG. 19). A flange 592 provides for attachment of the air column detector 552 to the mounting chamber body 552.

Figure 22:
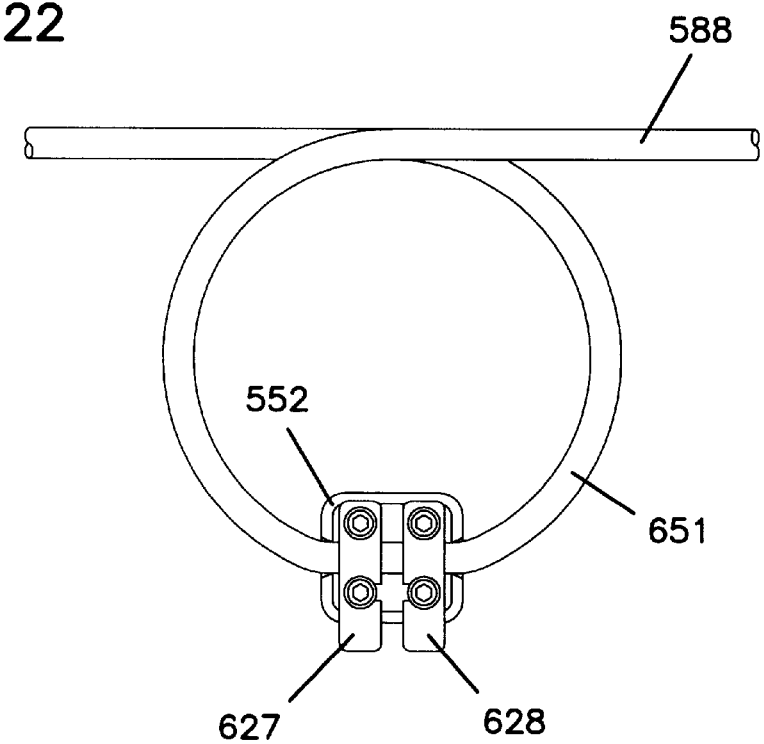
FIG. 22 is a schematic, side elevational view of an air column detector and tubing, in accordance with the present invention.

In reference now to FIG. 22, air column detector 552 is shown engaging fluid line 588 which has been wrapped around itself to form a loop 651. Although no particular theory with respect to this arrangement is asserted hereto, it is believed that by forming a loop 651 in fluid line 588, any air bubbles present within the fluid line 588 will be at a top side of the tube due to buoyancy resulting from gravitational forces and centrifugal forces due to the fluid flow. Gravitational forces push the bubble to the top side of the tube 588. Centrifugal forces push the bubble to the inside of the bend radius of the loop 651. By the section being at the bottom quadrant, both of these forces will be in the same direction pushing the bubble to the inside of the bend of the loop 651 and the top of the tube 588, independent of bend radius or fluid velocity. Thus, the bubble is forced to the top side of the tube 588. In certain arrangements, this tends to enhance the detection of any air bubbles by air column detector 552.

Again in reference to FIGS. 18 and 19, manifold holder 554 is provided to secure and hold a manifold, analogous to manifold 26, described above. A clamp structure 597 holds the manifold securely in place. Manifold holder 554 is mounted on a flange 594, which is secured to mounting chamber body 542. Manifold holder 554 is mounted on flange 594 in a slot 596, FIG. 20, to permit manifold holder 554 to slide back and forth within groove 596. This permits manifold holder 554 to accommodate different lengths of tubing 598, FIG. 19, from the outlet port housing 526 of the syringe 500.

Manifold holder 554 is configured and shaped to permit the manifold to snap in only one orientation. In this way, it can be assured that the manifold is always oriented in the same position relative to the manifold holder 554. Because of this, a sensor 599 can detect the position of the valve within the manifold. The sensor 599 is positioned in an integral part with the manifold 554. Sensor 599 preferably is an inductive type device. One type of sensor useable in the embodiment shown is an inductive sensor (part number IFRM 12P1701\L) available from Baumer.

Attention is again directed to FIG. 20. In FIG. 20, a pair of volume indicators 606, 607 are illustrated. Volume indicators 606, 607 are oriented relative to mounting chamber body 542, such that when syringe 500 is situated within mounting chamber body 542, the volume indicators 606, 607 provide a visual cue and indication for the level of fluid within the syringe body 502. As shown in FIG. 20, volume indicators 606, 607 each include a plurality of marks 608. As the fluid level within syringe body 502 changes, the user is able to visually detect where the level is by comparing it against the marks 608.

In accordance with the invention, a method for mounting or loading a syringe is provided. The method includes a step of positioning a syringe through a front aperture in a syringe holder arrangement. This includes sliding a syringe, such as syringe 500 in through the front end of a syringe holder arrangement 540. Using the components illustrated in the drawings, the syringe 500 is oriented to line up with the open end of the first end of the sleeve 548. That is, the second end 506 of the syringe 500 is aligned with the front of the sleeve 548, and the inlet port housing 570 is aligned with the slot 570. The rear, or second end 506, of syringe 500 (that is, the plunger receiving end) is first slid through the open end defined by the first end 568 of the sleeve 548. This is followed by the fluid-dispersement end of the sleeve, i.e., the first end 504 defining the flat face 516. The syringe 500 is slid into the interior of the sleeve 548.

Next, the door is closed. This blocks further access to the interior of the sleeve 548. This also provides for a stop surface, engagement surface, or abutting surface for the syringe 500 in order to absorb and sustain pressure load through the syringe 500. Specifically, the door member 564 is pivoted from one of its open positions, FIG. 18, to its closed position, FIG. 19. The user grasps the handle 566 and pivots the door to close the opening. As the door member 544 is being pivoted, the flat surface 564 of the door is slid relative to the flat face, 516, of the syringe 500, and relative to the first end portion 568 of the sleeve 548. As the door member 544 is moved into its closed position, the outlet tube housing 526 communicates with and slides through groove 565.

To unload the syringe 500 from the syringe holder arrangement 540, the above process is basically done in reverse. The door member 544 is pivoted from its closed position, FIG. 19, into one of its open positions, such as that illustrated in FIG. 18. The syringe 500 is then removed from the holder assembly 540. Specifically, the syringe 500 is slid from the interior of sleeve 548. The front end of syringe 500, that is, the end with the flat face 516, is slid out first, followed by the rear end, or second end 506.

Figure 21:
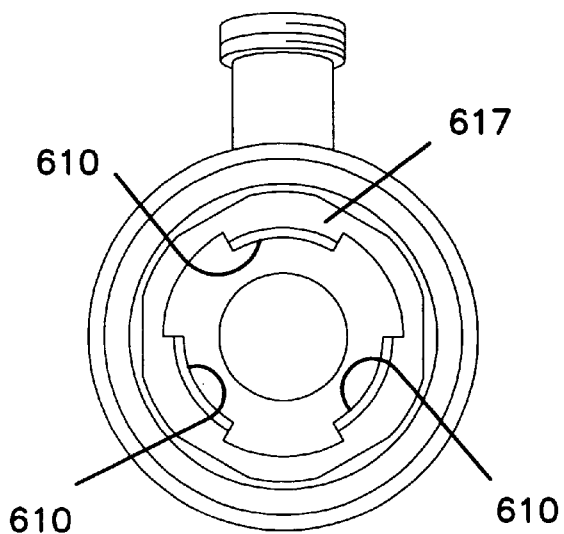
FIG. 21 is a rear side elevational view of the syringe depicted in FIG. 12, and analogous to FIG. 17, but with the plunger therein.

In accordance with the invention, the angiographic system described herein is constructed and arranged to ensure that syringe 500 is not re-used. That is, the angiographic system of the present invention includes features to ensure that the syringe 500 is disposed of after use with one patient and not accidentally re-used on a new, different patient. As embodied herein, the syringe 500 includes structure on its plunger support member 617 to ensure single use. As illustrated in FIG. 21, plunger support member 617 defines a plurality of projections or tabs 610. Tabs 610 project or extend radially inwardly toward the center or apex of the plunger 512. Tabs 610 are constructed of a flexible, deformable material, but also frangible or breakable, such that when the actuator engages plunger support member 617, tabs 610 are bent inwardly to accommodate the actuator. However, when syringe 500 is removed from the actuator, tabs 610 are broken, and the plunger support member 617 is destroyed. This prevents the syringe 500 from being re-used.

After a period of use, it may be desirable to remove the pressure containment sleeve 548 for cleaning. To do this, the locking assembly 574 in the rear plate 546 is shifted to disengage and release the locking pin 572. While the locking pin 572 is disengaged from the locking assembly 574, the sleeve 548 may be grasped at a first end 568 and slid out from its snug engagement with the mounting chamber body 542. At this point, the sleeve 548 may be cleaned.

To reinsert the sleeve 548, the sleeve 548 is slid back into secure, snug engagement with the mounting chamber 542. The locking assembly 574 is shifted to permit locking engagement with the locking pin 572.

We claim:

1. An injection system comprising:
    (a) a syringe including a barrel defining a pumping chamber, a longitudinal axis, and at least one port for providing fluid-flow communication with said pumping chamber; said barrel having a distal end and a proximal end:
        (i) said distal end including a flat wall section normal to said longitudinal axis;
        (ii) said syringe including a plunger constructed and arranged within said pumping chamber for reciprocal motion between a position adjacent to said proximal end and said distal end;
        (iii) said at least one port in said syringe including an inlet port and an outlet port; said outlet port being defined by said flat wall section;
        (iv) said syringe including an inlet port housing surrounding said inlet port, and an outlet port housing surrounding said outlet port; said outlet port housing protecting from said flat wall section; and
    (b) a syringe holder arrangement including:
        (i) a mounting chamber body constructed and arranged to hold said syringe; said mounting chamber body including a loading end for receipt of said syringe;
        (ii) a door member movable relative to said body to allow for selective opening and closing of said loading end of said mounting chamber body;
            (A) said door member defining a flat, planar surface for abutting engagement with said flat wall section of said syringe; and
            (B) said door member defining a slot for slidable communication with said outlet port housing.

2. An injection system according to claim 1, wherein:
    (a) said syringe holder arrangement further includes a pressure containment sleeve selectively mounted within said mounting chamber body for slidable receipt of said syringe;
        (i) said pressure containment sleeve defining open first and second, opposite ends; said first end being adjacent to said loading end of said mounting chamber body; said door member being selectively movable to open and close said first end.

3. An injection system according to claim 2, wherein:
    (a) said pressure containment sleeve defines an open channel for slidable communication with said inlet port housing.

4. An injection system according to claim 3, wherein:
    (a) said syringe holder arrangement further includes a plate mounted in covering relation to said second end of said pressure containment sleeve; said plate defining an aperture for allowing manipulation of said syringe plunger, when said syringe is positioned in said pressure containment sleeve.

5. An injection system according to claim 3, wherein:
(a) said syringe holder arrangement further includes a bottle-holder assembly constructed and arranged to mount a bottle in fluid-flow communication with said inlet port housing.

6. An injection system according to claim 1, including:
(a) an air column detector downstream from said syringe; and
(b) a tube providing fluid-flow communication between said syringe and said air column detector.

7. An injection system according to claim 1 wherein:
(a) the syringe flat wall section defines an interior portion and an exterior portion;
  (i) said exterior portion defining an end wall.

8. An injection system according to claim 7 wherein:
(a) said exterior portion is reinforced with a plurality of ribs; said ribs each having end portions terminating in a plane transverse to said longitudinal axis of the syringe;
  (i) said end portions of said ribs defining said flat face.

9. An injection system according to claim 7 wherein:
(a) said interior portion defines a cone-shaped surface.

10. An injection system according to claim 7 wherein:
(a) said barrel defines a top portion;
  (i) said inlet port being located in said top portion.

11. An injection system according to claim 10 wherein:
(a) said end wall defines a first portion and a second portion;
  (i) said first portion being adjacent to said top portion of said barrel;
  (ii) said second portion being adjacent to an end of said end wall opposite of said first portion;
  (iii) said outlet port being located in said second portion of said end wall.

12. An injection system according to claim 1 further including:
(a) a valve arrangement constructed and arranged to:
  (i) prevent liquid from flowing out of said pumping chamber through said inlet port when said plunger moves from said proximal end to said distal end; and
  (ii) allow air to flow out of said pumping chamber through said inlet port.

13. An injection system according to claim 12 wherein:
(a) said valve arrangement comprises a check valve.

14. An injection system according to claim 1, wherein:
(a) said syringe plunger includes a plunger support secured thereto.

15. An injection system according to claim 14, wherein:
(a) said plunger support includes at least one frangible tab member.

16. A method for mounting a syringe comprising steps of:
(a) positioning a syringe through a front aperture in a syringe holder arrangement;
(b) pivoting a door of the syringe holder arrangement to close the front aperture and about a front face of said syringe, said door including a planar surface; and
(c) said step of positioning a syringe includes:
  (i) providing a syringe having a first end at the syringe front face and defining a fluid port, and a second end slidably receiving a plunger, wherein said front face of said syringe is planar with an outlet port housing extending therefrom surrounding the fluid port;
  (ii) orienting said syringe through said front aperture such that said second end passes through said front aperture followed by said first end; and
  (iii) inserting said syringe into an interior of a pressure containment sleeve; and
(d) said step of pivoting a door includes sliding said planar surface of said door relative to said planar, front face of said syringe.

17. An injection system comprising:
(a) a syringe including a barrel defining a pumping chamber, a longitudinal axis, and at least one port for providing fluid-flow communication with said pumping chamber; said barrel having a distal end and a proximal end;
  (i) said distal end including a flat wall section normal to said central, longitudinal axis;
  (ii) said syringe including a plunger constructed and arranged within said pumping chamber for reciprocal motion between a position adjacent to said proximal end and said distal end;
  (iii) said at least one port in said syringe including an inlet port and an outlet port; said outlet port being defined by said flat wall section;
  (iv) said syringe including an inlet port housing surrounding said inlet port, and an outlet port housing surrounding said outlet port; said outlet port housing projecting from said flat wall section; and
(b) a syringe holder arrangement including:
  (i) a mounting chamber body constructed and arranged to hold said syringe; said mounting chamber body including a loading end for receipt of said syringe;
  (ii) a door member movable relative to said body to allow for selective opening and closing of said loading end of said mounting chamber body;
    (A) said door member defining a flat, planar surface for abutting engagement with said flat wall section of said syringe; and
    (B) said door member defining an opening for communication with said outlet port housing.

18. An injection system according to claim 17, wherein:
(a) said syringe holder arrangement further includes a pressure containment sleeve selectively mounted within said mounting chamber body for slidable receipt of said syringe;
  (i) said pressure containment sleeve defining open first and second, opposite ends; said first end being adjacent to said loading end of said mounting chamber body; said door member being selectively movable to open and close said first end.

19. An injection system according to claim 18, wherein:
(a) said pressure containment sleeve defines an open channel for slidable communication with said inlet port housing.

20. An injection system according to claim 19, wherein:
(a) said syringe holder arrangement further includes a plate mounted in covering relation to said second end of said pressure containment sleeve; said plate defining an aperture for allowing manipulation of said syringe plunger, when said syringe is positioned in said pressure containment sleeve.

21. An injection system according to claim 19, wherein:
(a) said syringe holder arrangement further includes a bottle-holder assembly constructed and arranged to mount a bottle in fluid-flow communication with said inlet port housing.

22. An injection system according to claim 17, including:
(a) an air column detector downstream from said syringe; and
(b) a tube providing fluid-flow communication between said syringe and said air column detector.

23. An injection system according to claim 22 wherein:
(a) said tube forms a loop, a portion of said loop engaging said air column detector.

24. A method for mounting a syringe comprising steps of:
(a) providing a syringe including a barrel defining a pumping chamber, a longitudinal axis, and at least one port for providing fluid-flow communication with said pumping chamber; said barrel having a distal end and a proximal end;
   (i) said distal end including a flat wall section normal to said central, longitudinal axis;
   (ii) said syringe including a plunger constructed and arranged within said pumping chamber for reciprocal motion between a position adjacent to said proximal end and said distal end;
   (iii) said at least one port in said syringe including an inlet port and an outlet port; said outlet port being defined by said flat wall section;
   (iv) said syringe including an inlet port housing surrounding said inlet port, and an outlet port housing surrounding said outlet port; said outlet port housing projecting from said flat wall section; and
(b) providing a syringe holder arrangement including a mounting chamber body and a door member movable relative to said body to allow for selective opening and closing of said front aperture of said mounting chamber body;
   (i) said door member defining a flat, planar surface for abutting engagement with said flat wall section of said syringe; and
   (ii) said door member defining an opening for communication with said outlet port housing;
(c) positioning said syringe through a front aperture of said mounting chamber body; and
(d) pivoting said door member to close said front aperture and abut a front face of said syringe.

25. A method for mounting a syringe according to claim 24 wherein
(a) said step of positioning a syringe includes inserting the syringe into an interior of a pressure containment sleeve.

26. A method for mounting a syringe according to claim 25 further comprising steps of;
(a) inserting an actuator into said plunger; and
(b) deforming said plunger to preclude further use by removing said actuator from said plunger.

* * * * *